United States Patent
Duan

(10) Patent No.: US 11,786,114 B2
(45) Date of Patent: Oct. 17, 2023

(54) SYSTEMS AND METHODS FOR LIQUID BIOPSY AND DRUG DELIVERY

(71) Applicant: AnX Robotica Corp, Pleasanton, CA (US)

(72) Inventor: Xiaodong Duan, Pleasanton, CA (US)

(73) Assignee: AnX Robotica Corp, Pleasanton, CA (US)

( * ) Notice: Subject to any disclaimer, the term of this patent is extended or adjusted under 35 U.S.C. 154(b) by 233 days.

(21) Appl. No.: 16/844,248

(22) Filed: Apr. 9, 2020

(65) Prior Publication Data

US 2020/0323422 A1 Oct. 15, 2020

Related U.S. Application Data

(60) Provisional application No. 62/831,447, filed on Apr. 9, 2019.

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00119* (2013.01); *A61B 1/00128* (2013.01);
(Continued)

(58) Field of Classification Search
CPC .............. A61B 1/0014; A61B 1/00147; A61B 1/00119; A61B 1/00128; A61B 1/00158; A61B 10/0045
See application file for complete search history.

(56) References Cited

U.S. PATENT DOCUMENTS

| 4,195,624 A * | 4/1980 | Douglas | A61B 1/2733 |
| | | | 600/114 |
| 4,198,960 A * | 4/1980 | Utsugi | A61B 1/0125 |
| | | | 600/104 |

(Continued)

FOREIGN PATENT DOCUMENTS

| CN | 103113606 A | 5/2013 |
| CN | 103304832 A | 9/2013 |

(Continued)

OTHER PUBLICATIONS

International Search Report dated Aug. 19, 2020, for PCT Application No. PCT/US2020/027422, filed on Apr. 9, 2020, 4 pages.

(Continued)

*Primary Examiner* — John P Leubecker
*Assistant Examiner* — Jae Woo
(74) *Attorney, Agent, or Firm* — Cooley LLP

(57) ABSTRACT

Systems for liquid biopsy and/or drug delivery may include a capsule endoscope and a tether coupled to the capsule endoscope. The tether may include a flexible member with a lumen in fluidic communication with a port configured to permit passage of fluid, and the port may be, for example, on the capsule endoscope or the tether. In methods for liquid biopsy and/or drug delivery, the capsule endoscope may be advanced into a gastrointestinal tract of a patient, and navigated to a region of interest, where a patient sample may be withdrawn and/or a therapeutic substance may be administered through the lumen (e.g., through the port).

22 Claims, 35 Drawing Sheets

(51) Int. Cl.
*A61B 10/00* (2006.01)
*A61M 31/00* (2006.01)
*A61B 1/015* (2006.01)

(52) U.S. Cl.
CPC .......... *A61B 1/00158* (2013.01); *A61B 1/015* (2013.01); *A61B 10/0045* (2013.01); *A61M 31/002* (2013.01); *A61B 2010/0061* (2013.01); *A61B 2562/162* (2013.01); *A61M 2210/1042* (2013.01)

(56) References Cited

U.S. PATENT DOCUMENTS

| | | | |
|---|---|---|---|
| 5,653,677 A * | 8/1997 | Okada | A61B 1/00016 600/112 |
| 5,840,251 A * | 11/1998 | Iwaki | A61B 1/121 422/36 |
| 8,235,888 B2 * | 8/2012 | Kawano | A61B 1/041 600/118 |
| 8,269,823 B2 * | 9/2012 | Hirakawa | A61B 1/04 348/65 |
| 9,339,174 B2 * | 5/2016 | Gilad | A61B 1/04 |
| 9,392,929 B2 * | 7/2016 | Bendele | A61B 1/00119 |
| 10,070,854 B2 | 9/2018 | Duan et al. | |
| 10,076,234 B2 | 9/2018 | Duan et al. | |
| 2002/0103417 A1 * | 8/2002 | Gazdzinski | A61B 1/00006 600/109 |
| 2003/0013938 A1 * | 1/2003 | Iddan | A61B 1/041 600/129 |
| 2003/0139647 A1 * | 7/2003 | Raz | A61M 31/007 600/104 |
| 2004/0267095 A1 * | 12/2004 | Miyake | A61B 1/0676 600/175 |
| 2005/0085697 A1 * | 4/2005 | Yokoi | A61B 1/273 600/160 |
| 2005/0267361 A1 * | 12/2005 | Younker | A61M 25/0105 600/423 |
| 2006/0193893 A1 | 8/2006 | Brown | |
| 2006/0235275 A1 * | 10/2006 | Rabinovitz | A61B 1/041 600/101 |
| 2007/0015961 A1 * | 1/2007 | Yamamoto | A61B 1/00147 600/102 |
| 2007/0049796 A1 * | 3/2007 | Fujikura | A61B 1/00089 600/116 |
| 2007/0118018 A1 * | 5/2007 | Gilad | A61B 1/051 600/160 |
| 2007/0260175 A1 * | 11/2007 | Segawa | A61J 7/0061 604/79 |
| 2007/0299309 A1 | 12/2007 | Seibel et al. | |
| 2008/0015413 A1 * | 1/2008 | Barlow | A61B 1/273 600/114 |
| 2008/0115606 A1 * | 5/2008 | Suzuki | A61B 1/0055 74/111 |
| 2008/0117291 A1 * | 5/2008 | Hirakawa | A61B 1/041 348/65 |
| 2008/0154093 A1 * | 6/2008 | Cho | A61B 1/00018 600/114 |
| 2008/0160477 A1 * | 7/2008 | Stookey | A61B 1/0684 433/31 |
| 2008/0167523 A1 * | 7/2008 | Uchiyama | A61B 5/073 600/114 |
| 2008/0167525 A1 | 7/2008 | Wakefield | |
| 2008/0177141 A1 * | 7/2008 | Wu | A61B 1/00147 600/112 |
| 2009/0018396 A1 * | 1/2009 | Takizawa | A61B 5/07 600/127 |
| 2009/0062614 A1 * | 3/2009 | Adzich | A61B 1/31 600/129 |
| 2010/0322866 A1 | 12/2010 | Rabinovitz | |
| 2011/0065987 A1 | 3/2011 | Mullick et al. | |
| 2011/0184293 A1 | 7/2011 | Rabinovitz et al. | |
| 2011/0254938 A1 * | 10/2011 | Asada | A61B 1/05 348/76 |
| 2011/0319639 A1 | 12/2011 | Wessig et al. | |
| 2012/0095391 A1 * | 4/2012 | Bendele | A61B 1/00128 604/26 |
| 2012/0101331 A1 * | 4/2012 | Gilad | A61B 1/041 600/114 |
| 2012/0165796 A1 * | 6/2012 | Ortiz | A61B 1/041 604/891.1 |
| 2014/0206016 A1 | 7/2014 | Lozano et al. | |
| 2014/0243598 A1 * | 8/2014 | Genier | A61B 1/00147 600/114 |
| 2015/0011829 A1 | 1/2015 | Wang et al. | |
| 2016/0235282 A1 | 8/2016 | Nakamura | |
| 2019/0099067 A1 | 4/2019 | Tseng | |
| 2020/0037862 A1 * | 2/2020 | Duan | A61B 1/015 |
| 2020/0196873 A1 * | 6/2020 | Ntziachristos | A61B 1/00147 |
| 2022/0022736 A1 | 1/2022 | Duan et al. | |

FOREIGN PATENT DOCUMENTS

| | | |
|---|---|---|
| CN | 107064131 A | 8/2017 |
| CN | 109813666 A | 5/2019 |
| CN | 109924937 A | 6/2019 |
| CN | 111202528 A | 5/2020 |
| CN | 111808916 A | 10/2020 |
| WO | WO-2019/171409 A1 | 9/2019 |

OTHER PUBLICATIONS

Written Opinion of the International Searching Authority dated Aug. 19, 2020, for PCT Application No. PCT/US2020/027422, filed on Apr. 9, 2020, 9 pages.

Chen, R. et al. (2006). "Quantitative Proteomic Profiling of Pancreatic Cancer Juice," Proteomics 6:3871-3879.

Eshleman, J.R. et al. (2015). "KRAS and Guanine Nucleotide-Binding Protein Mutations in Pancreatic Juice Collected from the Duodenum of Patients at High Risk for Neoplasia Undergoing Endoscopic Ultrasound." Clinical Gastroenterology and Hepatology 13:963-969.e4.

Farrell, J.J. et al. (2005). "Early Detection Markers in Pancreas Cancer," Cancer Biomarkers 1:157-175.

Fujiyama, Y. et al. (2020). "Promoter DNA Hypermethylation of the Cysteine Dioxygenase 1 (CDO1) Gene in Intraductal Papillary Mucinous Neoplasm (IPMN)," Annals of Surgical Oncology 27:4007-4016.

Hayakawa, H. et al. (2019). "Carcinoembryonic Antigen Level in the Pancreatic Juice Is Effective in Malignancy Diagnosis and Prediction of Future Malignant Transformation of Intraductal Papillary Mucinous Neoplasm of the Pancreas," Journal of Gastroenterology 54:1029-1037.

Majumder, S. et al. (2020). "Methylated DNA in Pancreatic Juice Distinguishes Patients with Pancreatic Cancer from Controls," Clinical Gastroenterology and Hepatology 18:676-683.e3.

Majumder, S. et al. (2019). "Novel Methylated DNA Markers Discriminate Advanced Neoplasia in Pancreatic Cysts: Marker Discovery, Tissue Validation, and Cyst Fluid Testing," The American Journal of Gastroenterology 114:1539-1549.

Mori, Y. et al. (2013). "A Minimally Invasive and Simple Screening Test for Detection of Pancreatic Ductal Adenocarcinoma Using Biomarkers in Duodenal Juice," Pancreas 42:187-192.

Nakamura, S. et al. (2019). "Pancreatic Juice Exosomal MicroRNAs as Biomarkers for Detection of Pancreatic Ductal Adenocarcinoma," Annals of Surgical Oncology 26:2104-2111.

Nakashima, A. et al. (2009). "Usefulness of Human Telomerase Reverse Transcriptase in Pancreatic Juice as a Biomarker of Pancreatic Malignancy," Pancreas 38:527-533.

Singhi, A.D. et al. (2018). "Preoperative Next-Generation Sequencing of Pancreatic Cyst Fluid Is Highly Accurate in Cyst Classification and Detection of Advanced Neoplasia," Gut 67:2131-2141.

Springer, S. et al. (2015). "A Combination of Molecular Markers and Clinical Features Improve the Classification of Pancreatic Cysts," Gastroenterology 149:1501-1510.

Tanaka, M. et al. (2019). "Cytologic Analysis of Pancreatic Juice Increases Specificity of Detection of Malignant IPMN-A Systematic Review," Clinical Gastroenterology and Hepatology 17:2199-2211. e21.

(56) References Cited

OTHER PUBLICATIONS

Tian, T. et al. (2017). "Pathomechanisms of Oxidative Stress in Inflammatory Bowel Disease and Potential Antioxidant Therapies," Oxidative Medicine and Cellular Longevity 2017:4535194.

Tobi, M. et al. (2013). "Prospective Markers for Early Diagnosis and Prognosis of Sporadic Pancreatic Ductal Adenocarcinoma," Digestive Diseases and Sciences 58:744-750.

Wang, J. et al. (2014). "Circulating MicroRNAs in Pancreatic Juice as Candidate Biomarkers of Pancreatic Cancer," Journal of Cancer 5:696-705.

Yu, J. et al. (2017). "Digital Next-Generation Sequencing Identifies Low-Abundance Mutations in Pancreatic Juice Samples Collected from the Duodenum of Patients with Pancreatic Cancer and Intraductal Papillary Mucinous Neoplasms," Gut 66:1677-1687.

Non-Final Office Action dated Sep. 6, 2022, for U.S. Appl. No. 17/384,101, filed Jul. 23, 2021, 11 pages.

Chinese Office Action dated Jun. 10, 2022, for Application No. 202010725938.5, filed on Jul. 23, 2021, 14 total pages (with English Translation).

Extended European Search Report dated Dec. 5, 2022, for EP Application No. 20 787 566.7, filed on Apr. 9, 2020, 8 pages.

International Search Report dated Oct. 20, 2021, for PCT Application No. PCT/US2021/108258, filed on Jul. 23, 2021, 7 pages (with English Translation).

Non-Final Office Action dated Feb. 6, 2023, for U.S. Appl. No. 17/384,101, filed Jul. 23, 2021, 13 pages.

Zhao, X.-R. et al. (2016). "Highly sensitive fluorescence detection of trypsin based on gold nanoparticle probes," Anal. Methods 8:393-400.

\* cited by examiner

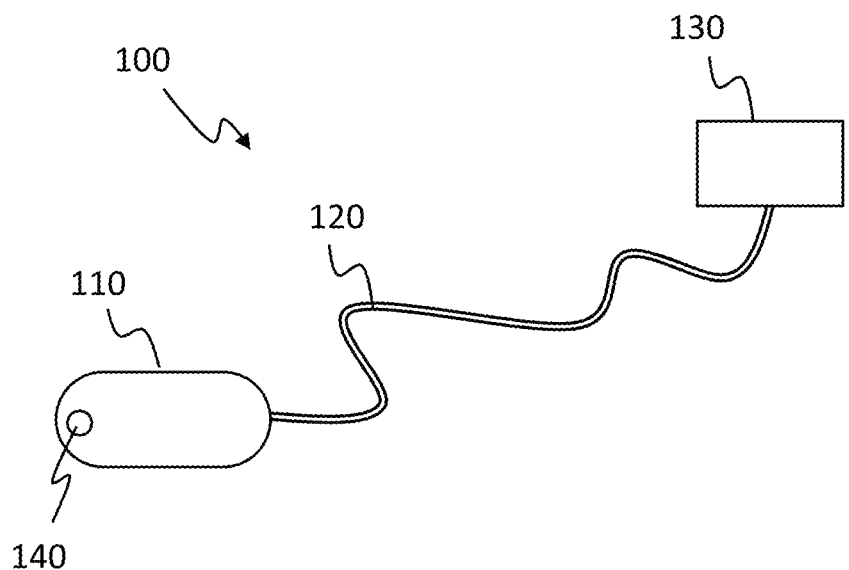
FIG. 1A
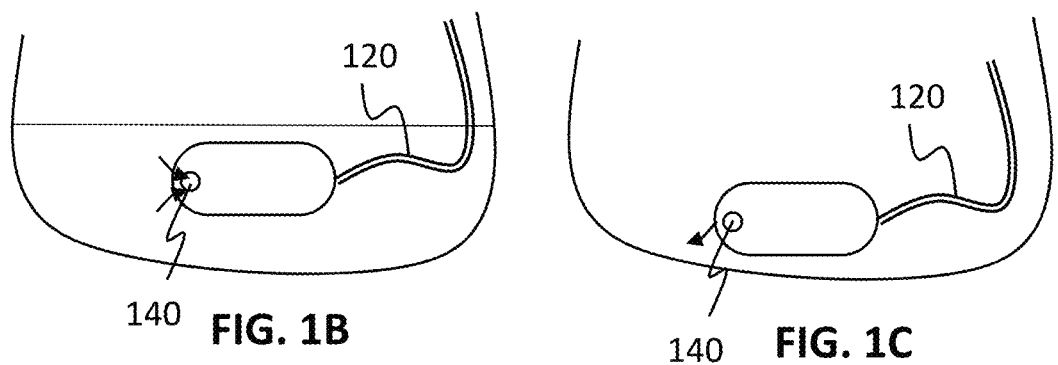
FIG. 1B FIG. 1C

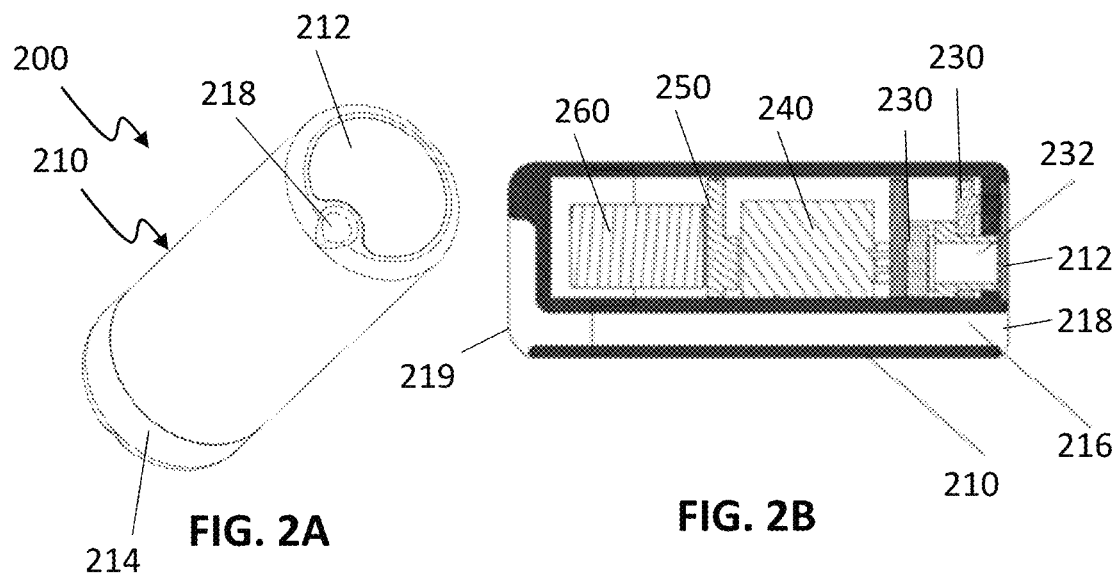
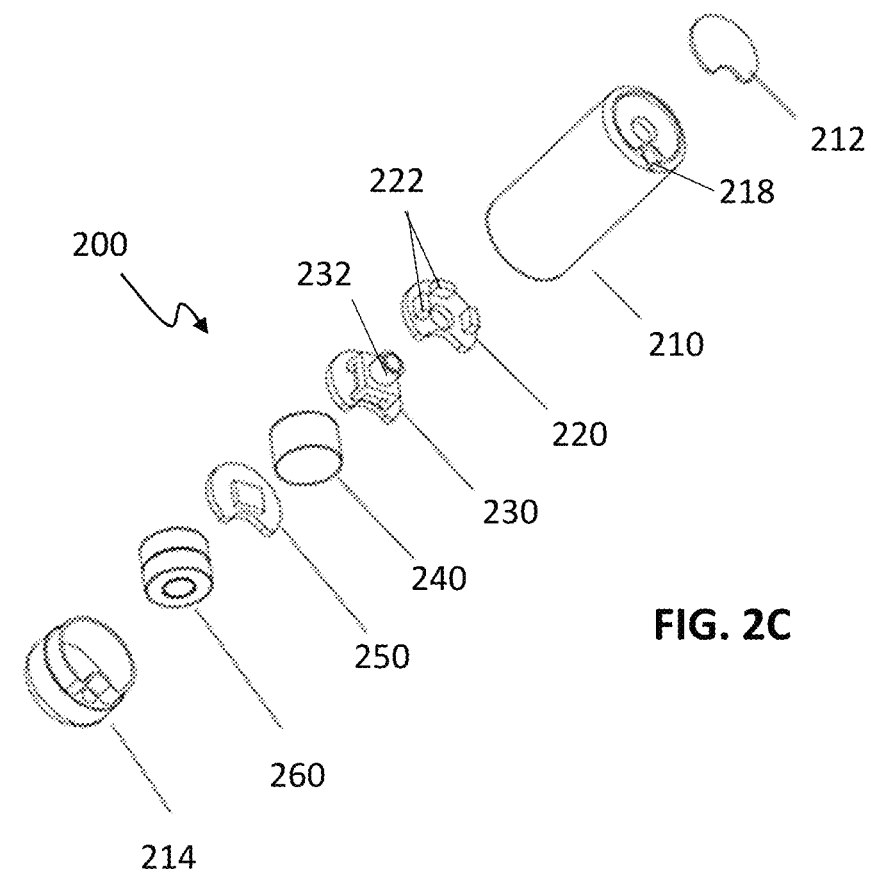

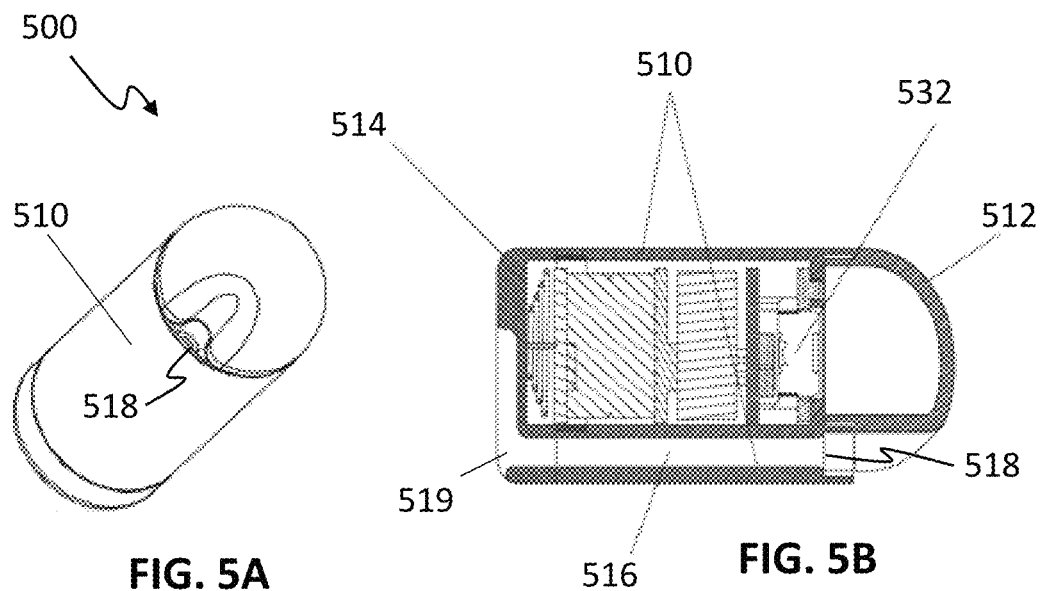
FIG. 5A
FIG. 5B
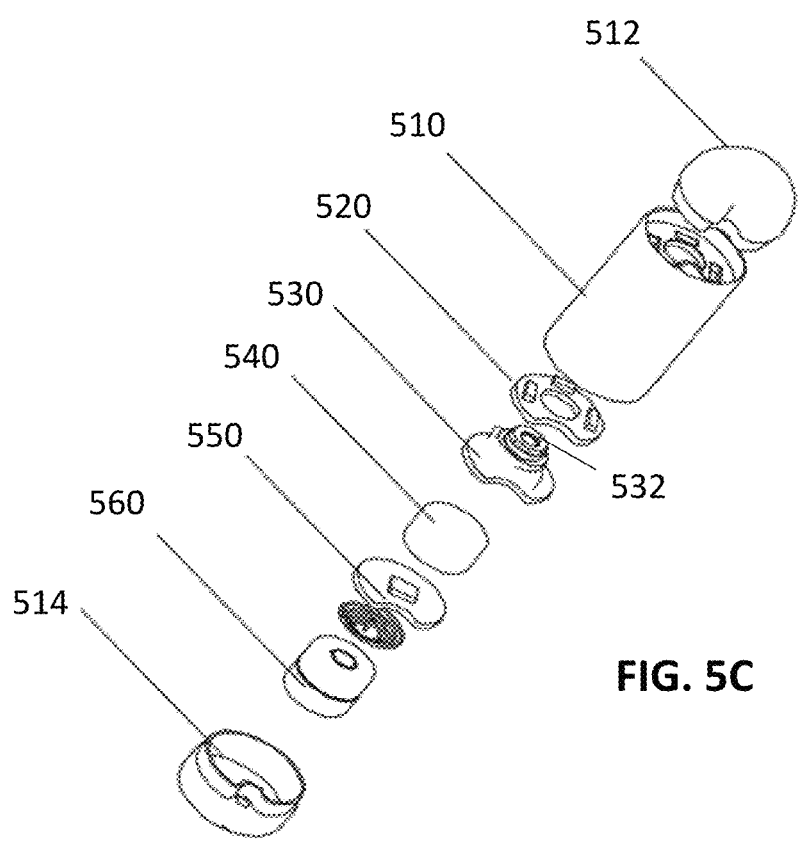
FIG. 5C

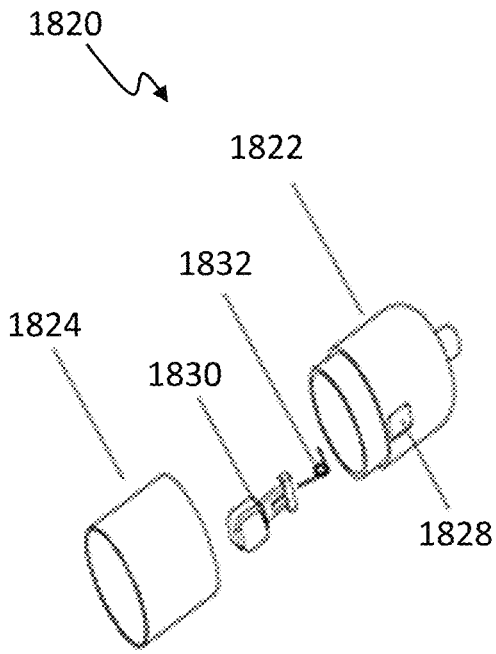
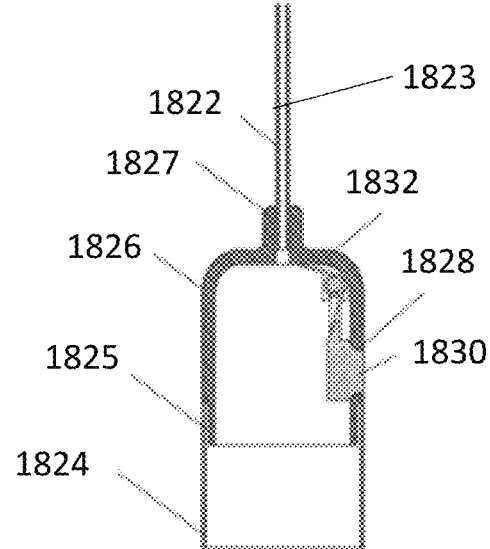
FIG. 18A
FIG. 18B
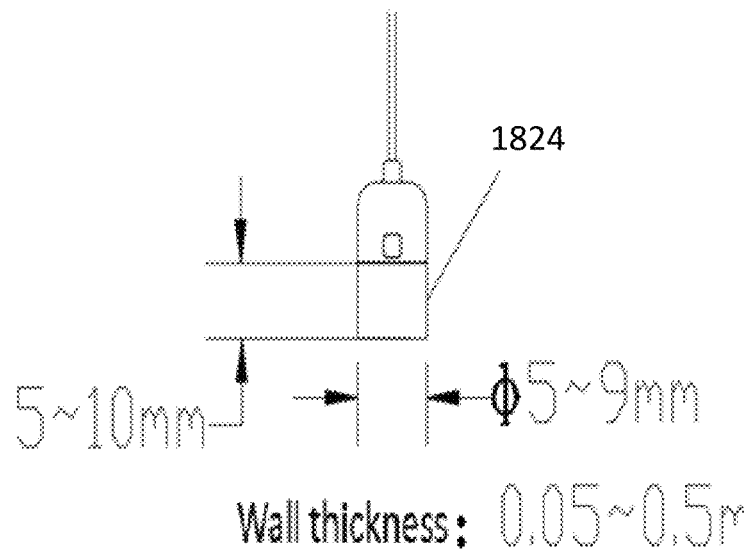
FIG. 18C

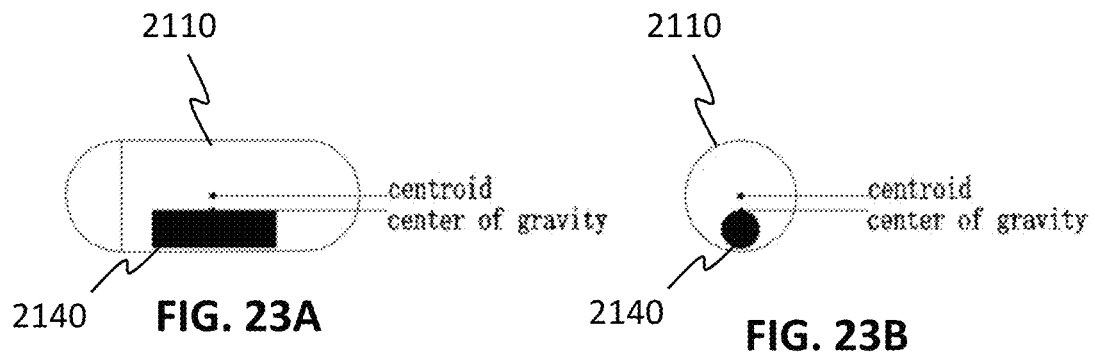
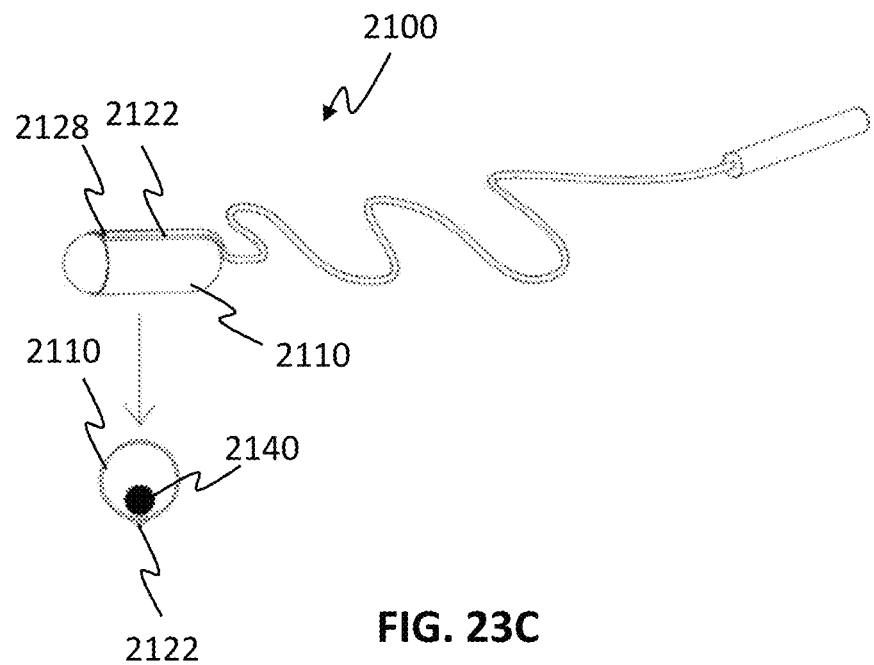

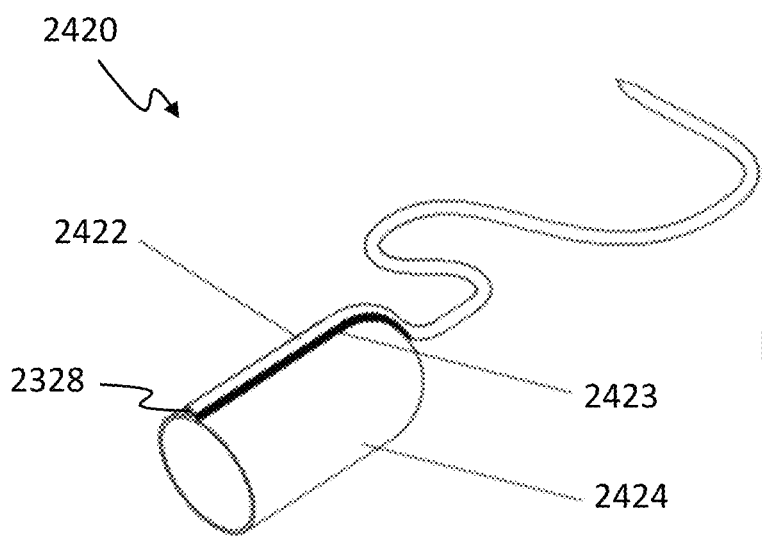
FIG. 24A
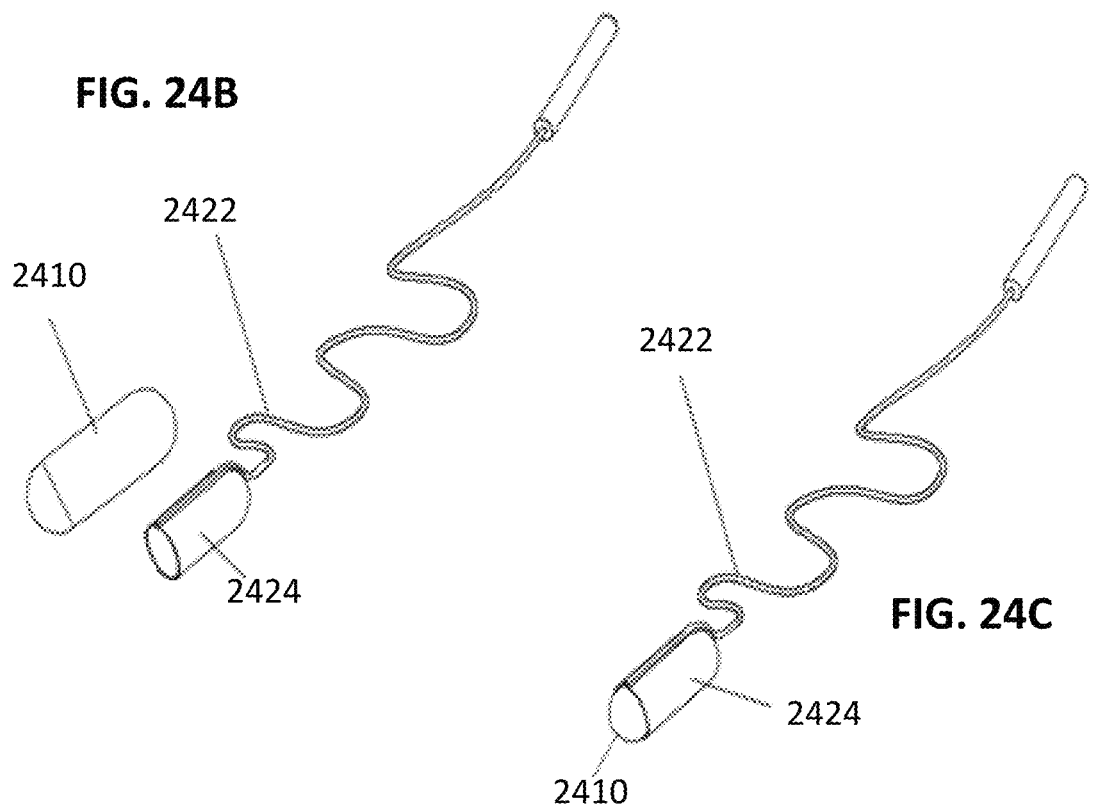
FIG. 24B
FIG. 24C

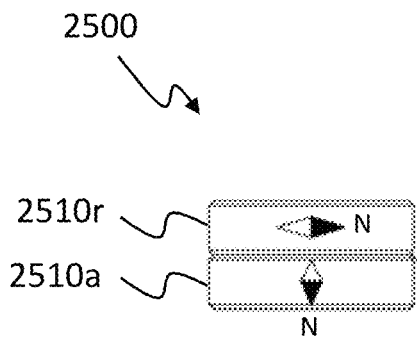 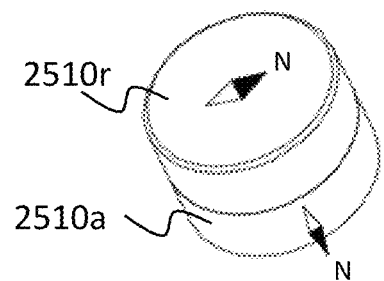
FIG. 25A  FIG. 25B
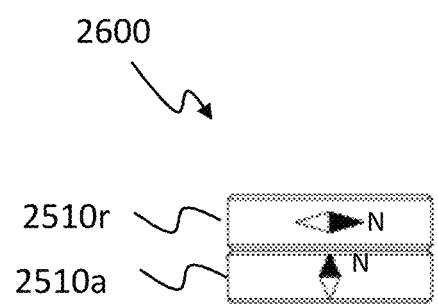 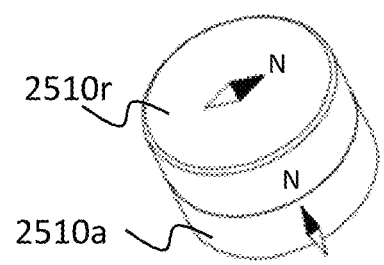
FIG. 26A  FIG. 26B

SYSTEMS AND METHODS FOR LIQUID BIOPSY AND DRUG DELIVERY

CROSS-REFERENCE TO RELATED APPLICATIONS

This application claims priority to U.S. Patent Application Ser. No. 62/831,447 filed on Apr. 9, 2019, which is hereby incorporated by reference in its entirety.

TECHNICAL FIELD

This invention relates generally to the field of medical treatment and more specifically to biopsy and drug delivery for patients.

BACKGROUND

During the course of medical treatment of a patient, it may be important to directly access regions of interest in the patient, such as for obtaining bodily samples (e.g., for diagnosis and/or monitoring of treatment progress of an afflicted region) or administering therapeutic agents (e.g., to lesions). However, certain body cavities and other internal areas of a patient may be difficult to access. For example, at least some portions of the gastrointestinal tract (e.g., esophagus, stomach, small intestine, large intestine, etc.) or other internal organs (e.g., pancreas, gallbladder, etc.) may be located relatively deep into the body of the patient. Accessing these areas for tissue interaction may require special tools and/or risk causing tissue damage and endangering patient health.

As an illustrative example, it may be desirable to obtain a biopsy of pancreatic juice from a patient, such as to assess presence of mutations suggesting presence of pancreatic cancer. Conventional methods for obtaining a biopsy of pancreatic juice include endoscopic retrograde cholangiopancreatography (ERCP) and endoscopic ultrasound-guided fine-needle aspiration (EUS-FNA). However, these methods may lead to complications such as pancreatitis, infections, hemorrhage, and bowel perforation.

Accordingly, there is a need for new and improved non-invasive systems and methods for accessing regions of interest in a patient.

SUMMARY

Generally, in some variations, a system for accessing a patient includes a capsule endoscope comprising an imaging system and a port configured to permit passage of fluid. The system may further include a tether coupled to the capsule endoscope and include a flexible member, where the flexible member includes a lumen in fluidic communication with the port. Furthermore, in some variations the tether may include a clamp configured to engage the capsule endoscope, and the clamp may be configured to releasably engage the capsule endoscope. The system may further include a pressure source and/or vacuum source (e.g., syringe, pump, etc.) arranged in fluidic communication with the lumen.

In some variations, the capsule endoscope may be magnetically controllable, such as with an external magnetic control system. The capsule endoscope may include one or more suitable compartments or other structures for conveying fluid between the lumen and port. In some variations, the compartment may include an elongated channel having a proximal end in fluidic communication with the lumen and a distal end in fluidic communication with the port. The elongated channel may, for example, extend from a proximal portion of the capsule endoscope to a distal portion of the capsule endoscope. In some variations, the compartment may include a chamber. The chamber may, for example, be in a proximal portion of the capsule endoscope.

Additionally, generally in some variations, a system for accessing a patient includes a capsule endoscope including an imaging system, and a tether including a clamp configured to engage the capsule endoscope, and a flexible member including a lumen, where the clamp includes a port in fluidic communication with the lumen. In some variations, the imaging system may include a first lens on a proximal portion of the capsule endoscope, and/or a second lens on a distal portion of the capsule endoscope. The endoscope may be magnetically controllable. Furthermore, in some variations the tether may include a clamp configured to engage the capsule endoscope, and the clamp may be configured to releasably engage the capsule endoscope. The system may further include a pressure source and/or vacuum source (e.g., syringe, pump, etc.) arranged in fluidic communication with the lumen.

In some variations, the clamp of the tether may include a sheath configured to surround at least a portion of the capsule endoscope. The clamp may, in some variations, include an anchor member coupling the sheath and the flexible member of the tether. In some variations, the port may be on the anchor member and axially offset from a proximal portion of the capsule endoscope. For example, the anchor may include one or more arcuate structures coupled to the sheath to provide an offset or a window region between the port and the capsule endoscope. Furthermore, in some variations, the clamp may include a housing defining a chamber between the sheath and the flexible member, and the port may be in the housing. In some of these variations, the housing may further include a valve (e.g., one-way valve).

Additionally, generally in some variations, a system for accessing a patient includes a capsule endoscope including an imaging system having a field of view, and a tether including a flexible member having a port. The port may be within the field of view of the imaging system, and the port may be configured to permit passage of fluid. In some variations, the imaging system may include a lens on a proximal portion of the capsule endoscope and/or a distal portion of the capsule endoscope. In some variations, the capsule endoscope may be magnetically controllable. The system may further include a pressure source and/or vacuum source (e.g., syringe, pump, etc.) arranged in fluidic communication with the lumen.

The flexible member may be coupled to the capsule endoscope in some variations. For example, the capsule endoscope may include a housing and at least a longitudinal portion of the flexible member may be coupled to the housing.

Additionally or alternatively, in some variations the flexible member may be coupled to a portion of the tether, such as a clamp that is configured to engage the capsule endoscope. In these variations, at least a longitudinal portion of the flexible member may be coupled to the clamp. The clamp may, for example, be configured to releasably engage the capsule endoscope.

Generally, in some variations, a method of accessing a patient includes advancing a capsule endoscope into a gastrointestinal tract of a patient, where the capsule endoscope is coupled to a tether including a flexible member with a lumen, positioning the capsule endoscope at a region of interest, and administering a therapeutic substance to the region of interest through the lumen. Administering the therapeutic substance may, for example, including administering the therapeutic substance through a port in fluidic communication with the lumen. For example, the port may be on the capsule endoscope or the tether. The therapeutic substance may be administered at least in part by applying positive pressure to the lumen. In some variations, the method may further include separating the capsule endoscope from the tether, then administering the therapeutic substance after separating the capsule endoscope from the tether.

Additionally, in some variations, a method of accessing a patient includes advancing a capsule endoscope into a gastrointestinal tract of a patient, where the capsule endoscope is coupled to a tether including a flexible member with a lumen, positioning the capsule endoscope at a region of interest, and withdrawing a patient sample from the region of interest through the lumen. Withdrawing a patient sample may, for example, including withdrawing a patient sample through a port in fluidic communication with the lumen. For example, the port may be on the capsule endoscope or the tether. The patient sample may be withdrawn at least in part by applying negative pressure to the lumen. In some variations, the method may further include separating the capsule endoscope from the tether, then withdrawing a patient sample after separating the capsule endoscope from the tether.

BRIEF DESCRIPTION OF THE DRAWINGS

FIG. 1A is an illustrative schematic depicting an exemplary variation of a capsule endoscope system for accessing a patient. FIG. 1B is an illustrative schematic depicting a method for performing liquid biopsy using an exemplary variation of a capsule endoscope system for accessing a patient. FIG. 1C is an illustrative schematic depicting a method for performing drug delivery using an exemplary variation of a capsule endoscope system for accessing a patient.

FIGS. 2A-2C are perspective, longitudinal cross-sectional, and exploded views, respectively, of an exemplary variation of a capsule endoscope with a port at its distal portion.

FIGS. 5A-5C are perspective, longitudinal cross-sectional, and exploded views, respectively, of an exemplary variation of a capsule endoscope with a port at its distal portion.

FIGS. 18A and 18B are exploded and side cross-sectional schematic views, respectively, of an exemplary variation of a tether with a housing and port. FIG. 18C is an illustrative schematic depicting exemplary dimensional ranges of aspects of the tether variation depicted in FIGS. 18A and 18B.

FIGS. 23A and 23B are side and cross-sectional schematic views, respectively, of an exemplary variation of a capsule endoscope having a biased center of gravity. FIG. 23C is an illustrative schematic depicting the capsule endoscope variation depicted in FIGS. 23A and 23B in combination with the tether variation depicted in FIGS. 21A and 21B.

FIG. 24A is an illustrative schematic of another exemplary variation of a tether including a clamp configured to engage or receive a capsule endoscope. FIGS. 24B and 24C are illustrative schematics of a tethered system including the tether variation depicted in FIG. 24A.

FIGS. 25A and 25B are side and perspective schematic views, respectively, of one exemplary variation of an internal magnet assembly in a capsule endoscope.

FIGS. 26A and 26B are side and perspective schematic views, respectively, of another exemplary variation of an internal magnet assembly in a capsule endoscope.

DETAILED DESCRIPTION

Figure 2D:
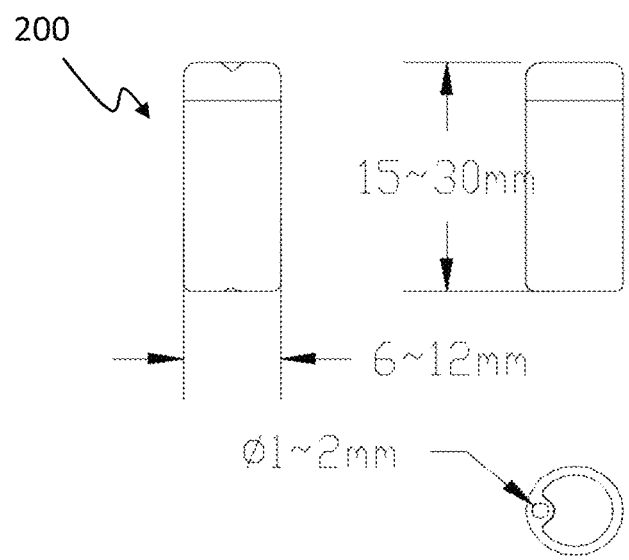
FIG. 2D is an illustrative schematic depicting exemplary dimension ranges of the capsule endoscope depicted in FIGS. 2A-2C.

Non-limiting examples of various aspects and variations of the invention are described herein and illustrated in the accompanying drawings.

Generally, a system for accessing a patient (e.g., for liquid biopsy, drug delivery, etc.) may include a capsule endoscope and a tether coupled to the capsule endoscope. The capsule endoscope may, for example, include an imaging system that enables visualization (e.g., through still images, videos, etc.) of its surroundings. In some variations, the capsule endoscope may include one or more magnets such that the capsule endoscope may be controlled at least in part through a magnetic control system. The tether coupled to the capsule endoscope may include a flexible member with a lumen in fluidic communication with a port configured to permit passage of fluid, and the port may be, for example, on the capsule endoscope or the tether. In some variations, the flexible member may be coupled to the capsule endoscope directly, while in some variations, the flexible member may be coupled to the capsule endoscope via a clamp or other suitable intervening attachment.

For example, as shown in the exemplary schematic of FIG. 1A, a system 100 for accessing a patient may include a capsule endoscope 110 and a tether 120 including a flexible member coupled to the capsule endoscope. A pressure modulator 130, such as a pressure source or a vacuum source (e.g., syringe or pump), may be coupled to the tether so as to be in fluidic communication with a lumen of the flexible member and a port 140 that permits passage of fluid. Although the port 140 is shown in FIGS. 1A-1C as located on a distal portion of the capsule endoscope 110, it should be understood that in other variations, a port 140 may additionally or alternatively be located on other suitable portions of the capsule endoscope (e.g., a proximal portion of the capsule endoscope 110, a central portion of the capsule endoscope 110). Furthermore, in other variations at least one port may be located on the tether (e.g., on distal portion of the flexible member, on a clamp member of the tether, etc.). Other exemplary variations of the system, including examples of suitable arrangements for the port, are described in further detail below.

During use, the capsule endoscope may be advanced into a body cavity such as a gastrointestinal tract of a patient, with the tether trailing the capsule endoscope and extending external to the patient. The capsule endoscope may be advanced to a region of interest. The imaging system of the capsule endoscope may aid such navigation by, for example, providing visibility to an operator of the location of the capsule endoscope relative to the region of interest, the surrounding conditions near the capsule endoscope (e.g., for determining whether sufficient patient fluid in the body cavity for biopsy is present, for determining whether lesions or other diseased conditions are present, etc.). At the region of interest, a liquid biopsy or patient sample may be withdrawn from the patient through the port. For example, a vacuum source (e.g., syringe with withdrawn plunger, vacuum pump, etc.) may be coupled to the tether so as to introduce a negative pressure in the tether, which draws a liquid biopsy through the port as shown in FIG. 1B, through the tether, and to a collection point external to the patient. Additionally or alternatively, a pressure source (e.g., syringe with depressed plunger, pressure pump, etc.) may be coupled to the tether so as to introduce a positive pressure in the tether, which may urge a therapeutic substance (e.g., drug) through the tether and through the port to a region of interest (e.g., lesion) as shown in FIG. 1C. Other exemplary aspects of methods for using the system are described below.

Generally, the systems and methods described herein are comfortable and non-invasive to a patient, thereby reducing risk of dangerous complications such as infection, hemorrhage, and perforations. The systems and methods may be used in various applications for liquid biopsy and/or drug delivery. For example, the system may be used to draw pancreatic juice from a patient, or to sample intestinal flora in a patient. As another example, the system may be used to deliver drugs to lesions (e.g., in the esophagus) or to one or more regions of interest in the small intestine, such as to treat irritable bowel disorder (IBD) or other conditions. As yet another example, drug delivery may be concurrent with controlled movement of the capsule endoscope, such as for spraying or otherwise releasing a drug across a surface (e.g., internal surface region of the stomach).

Capsule Endoscope

Generally, the capsule endoscope may include a housing enclosing various endoscope components. For example, the capsule endoscope may include an imaging system, an illumination system, a communication module, and/or a power source. In some variations, the capsule endoscope may include one or more magnets for facilitating movement control (e.g., navigation, rotation, etc.) of the capsule endoscope by a magnetic control system external to the patient, as described in further detail below. Other electronics, such as a posture sensor (e.g., gyroscope), controller(s), etc. may further be included in the housing. Furthermore, in some variations, the capsule endoscope may include a port configured to permit passage of fluid in and/or out of the capsule endoscope. As described in further detail below, the port may be located, for example, on a distal end of the capsule endoscope or a proximal end of the capsule endoscope (or other suitable location). In some of these variations, the capsule endoscope may include a center of gravity that is biased toward the port, such that the gravity tends to help the port be submerged in fluid for obtaining liquid biopsy. Additionally or alternatively, the capsule endoscope may include a buoyant element that is on an opposite side or end of capsule endoscope relative to the port, such that the buoyant element tends to help the port be submerged in fluid for obtaining liquid biopsy.

Generally, the housing may provide an overall casing and shape for the capsule endoscope. The housing may have rounded or beveled edges so as to reduce risk of tissue damage when the capsule endoscope is advanced through a body cavity (e.g., gastrointestinal tract) of a patient. The housing may include one or more interior volumes within which the endoscope components may reside. These volumes may be fluid-tight sealed, such as through mechanical interfit (e.g., press fit) components and/or epoxy, etc. The housing may, for example, include a biocompatible plastic that is injection-molded or formed in any suitable manner.

The imaging system of the capsule endoscope may, for example, assist navigation of the capsule endoscope within the patient and/or enable visual assessment of surrounding patient tissue (e.g., confirmation of presence of fluid for available for biopsy, identification of lesions, etc.). The imaging system may include one or more suitable image sensors, such as CMOS image sensors, for obtaining images of the environment around the capsule endoscope. For example, one or more image sensors may have a field of view including the environment around the capsule endoscope. The illumination system may include one or more suitable light sources, such as light-emitting diodes (LEDs) arranged to illuminate a field of view of the imaging system.

Control signals and/or image data may be communicated to and from the capsule endoscope through a communication module in the capsule endoscope. The communication module may, for example, be a wireless communication module including a suitable RF antenna arrangement on a processing circuit board. In other variations, the capsule endoscope may alternatively include a communication module configured to communicate via a wired connection which may, for example, travel external to the patient via the tether.

One or more power sources function to supply power to the various capsule components. The power source may, for example, include a suitable battery. In some variations, a controller may operate the power source to provide different power states for the capsule endoscope, such as an inactive state in which the capsule endoscope draws a low amount of power (e.g., for storage, transport, etc.) and an active state in which the capsule endoscope utilizes a higher amount of power (e.g., for imaging).

In some variations, the capsule endoscope may include an opto-electronic switching starter installed near the illumination system. The opto-electronic switching starter may be arranged adjacent the light sources and include, for example, a field effect transistor (FET) and an electronic switch connected with the FET. When light is generated by the illumination unit, the light may shine on the opto-electronic switching starter, causing the electronic switch to be turned on or activated. This activation of the electronic switch may effectively activate the capsule endoscope from a low power state (e.g., during advancement of the capsule endoscope) to an operational power state (e.g., for imaging of a region of interest). For example, the activation of the electronic switch may generate an opening pulse that causes the power source to electronically connect to other components of the capsule endoscope such as the imaging system, the wireless communication module 250, etc. This and other exemplary aspects of the capsule endoscope are described in further detail in U.S. Patent Publication No. 2015/0011829, which is hereby incorporated in its entirety by this reference.

Various exemplary variations of capsule endoscopes having different arrangements of endoscope components are described in further detail below.

FIGS. 2A-2C depict an exemplary variation of a capsule endoscope 200 including a port 218 at a distal end of the capsule endoscope 200. As shown in FIGS. 2B and 2C, the capsule endoscope 200 may include a housing 210 that encloses various endoscope components, such as an imaging system 230, an illumination system 220, one or more magnets 240, a wireless communication module 250, and/or one or more power sources 260. Except as described below, the imaging system 230, the illumination system 220, the wireless communication module 250, and one or more power sources 260 may be similar to those described above. In some variations, other electronics such as a posture sensor (e.g., gyroscope), controller(s), etc. may further be included in the housing 210.

As shown in FIG. 2D, the housing 210 may be generally cylindrical, with rounded or beveled edges. The housing 210 may include a generally cylindrical central section including one or more internal volumes for containing endoscopic components. The central section may be capped at its proximal (rear) and distal (front) ends with a proximal cover 214 and a distal cover 212. As shown in FIGS. 2A-2D the proximal and distal covers may be substantially flat or planar. The proximal cover 214 and/or distal cover 212 may include an optically transparent material (e.g., acrylic) that enables visibility and/or illumination of the environment external to the capsule endoscope by the imaging system and illumination system within the capsule endoscope. Exemplary dimensions of the housing are a length of between about 15 mm to about 30 mm, and a diameter of between about 6 mm to about 12 mm. Such dimensions may, for example, be small enough to allow passage of the capsule endoscope into the gastrointestinal tract without substantial discomfort or pain, but large enough to house the endoscope components.

As described above, the capsule endoscope 200 may include one or more magnets 240. The one or more magnets 240 may be controllable by an external magnetic control system, as further described below. The one or more magnets 240 may, for example, be configured to allow manipulation of the capsule endoscope with 6 degrees of freedom (DOF), including translational motion along three perpendicular axes, as well as rotational motion along three perpendicular axes (yaw, pitch, roll). In some variations, however, the capsule endoscope 200 may omit magnets 240. For example, instead of being controlled by an external magnetic control system, the capsule endoscope may be advanced through peristalsis in the gastrointestinal tract of a patient.

The imaging system 230 and/or illumination system 220 may be similar to the imaging and illumination systems described above. For example, as shown in FIG. 2C, an illumination system 220 may include three LEDs 222 arranged on a circuit board to emit light (e.g., white light) through a transparent window in the distal cover 212 of the housing 210. Although three LEDs are shown in FIG. 2C, it should be understood that any suitable number (e.g., one, two, four, five or more) may be included in the illumination system 220. The LEDs 222 may be distributed around a lens 232 of the imaging system 230, such as to provide visibility in the field of view of the imaging system 230. Furthermore, the LEDs 222 and the imaging system 230 may be arranged proximate the port 218 (e.g., on a distal portion of the capsule endoscope), such that the illuminated field of view may provide visibility into the environment immediately around the port 218. Accordingly, the imaging system 230 may be configured to provide images that confirm, for example, that the port 218 is submerged in a sufficient amount of patient fluid for obtaining a sample through the port 218, and/or that the port 218 is sufficiently near a region of interest (e.g. lesion) for delivering a drug to through the port 218 to the region of interest.

Figure 3:
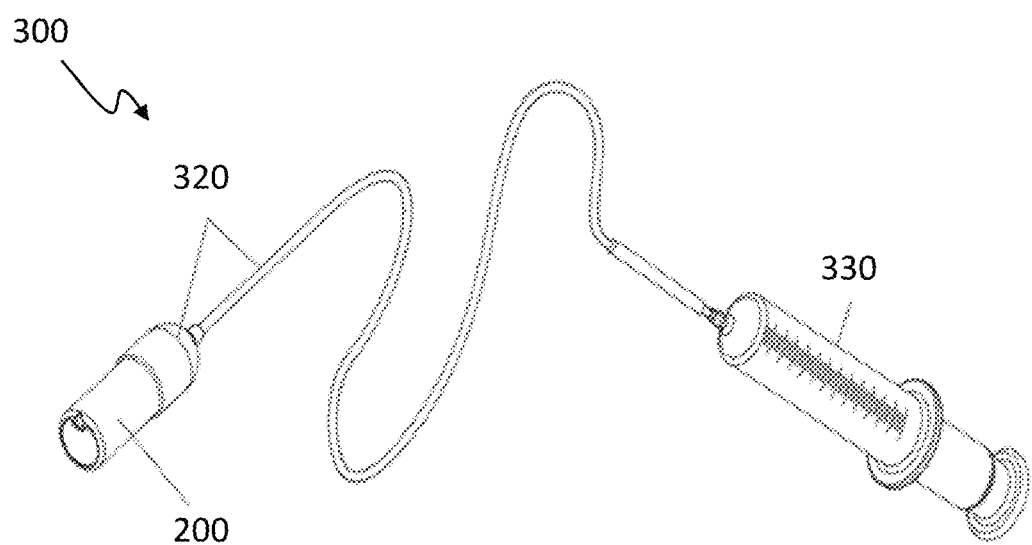
FIG. 3 is an illustrative schematic depicting an exemplary variation of a tethered system including the capsule endoscope variation depicted in FIGS. 2A-2C.

As shown in FIG. 3, in a system 300, the capsule endoscope 200 may be coupled to a tether 320 including a flexible member having a lumen, and the tether 320 may be coupled to a pressure modulator 330 (e.g., pressure source or vacuum source, such as a syringe or pump). The tether 320 may include a lumen, such as in a flexible member, and may be coupled to the capsule endoscope 200 in any suitable manner such as directly (e.g., with epoxy, with a barb fitting or other fitting) or via a clamp, as described in further detail below.

In some variations, the capsule endoscope 200 may include a compartment 216 that is defined separately from the one or more electronics compartments containing the electronics components described above. The compartment 216 may be in fluidic communication between a lumen of the tether 320 and the port 218, so as to enable passage of fluid between the port and a portion of the tether 320 external to the patient (and vice versa). In other words, the compartment 216 may, in combination with the lumen of the tether 320 and the port 218, form a conduit. For example, as shown in FIGS. 2A-2C, the compartment may include an elongated channel that has a proximal end in fluidic communication with the lumen of the tether 320, and a distal end in fluidic communication with the port 218. The elongated channel may extend from a proximal portion of the capsule endoscope to a distal portion of the capsule endoscope. The elongated channel may, for example, terminate at an opening 219 in the rear cover 214 that adjoins with the tether 320. The channel may have a generally circular cross-section, but may alternatively include any suitable cross-sectional shape (e.g., oval or elliptical, etc.). In some variations, at least some components in the one or more electronics compartments may be sized and/or shaped to accommodate cross-sectional area of the channel extending along the capsule endoscope. For example, as shown in FIG. 2C, the circuit boards of the wireless communication module 240, the imaging system 230 and/or the illumination system 220 may be generally crescent-shaped, with crescent-shaped cutouts that accommodate the cross-sectional area of the channel.

In some variations, the capsule endoscope 200 may have a center of gravity that is biased toward the distal end of the capsule endoscope, such that the gravity may tend to help the submersion of the port 218 (located at the distal portion of the capsule endoscope) in pooled fluid for obtaining liquid biopsy. The center of gravity may be adjusted appropriately by, for example, distributing more weight (e.g., magnet, which may be relatively dense) toward the distal end of the capsule endoscope 200. However, the center of gravity may additionally or alternatively be adjusted in other suitable ways, such as a non-uniform distribution of housing material (e.g., thickness of the housing may be greater, or the housing may have a heavier material at a distal end). Additionally or alternatively, a relatively buoyant element or feature (e.g., an air-containing compartment) may be located on an opposing end of the capsule endoscope relative to the port 218.

Figure 4A:
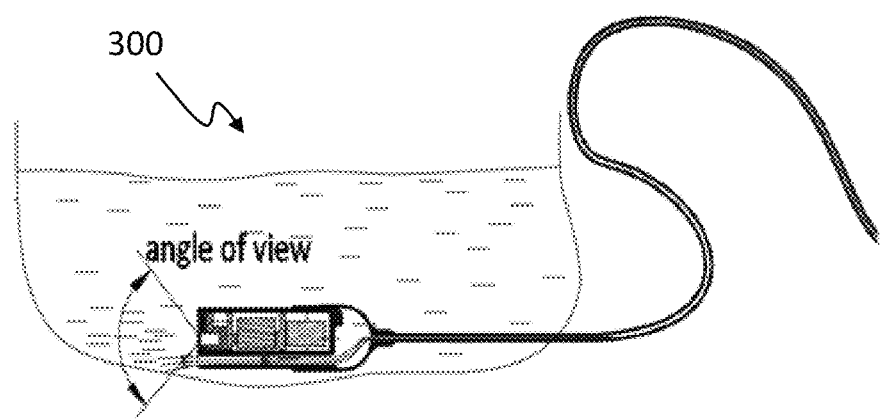
FIG. 4A is an illustrative schematic depicting a method for performing liquid biopsy using the capsule endoscope variation depicted in FIGS. 2A-2C.
Figure 4B:
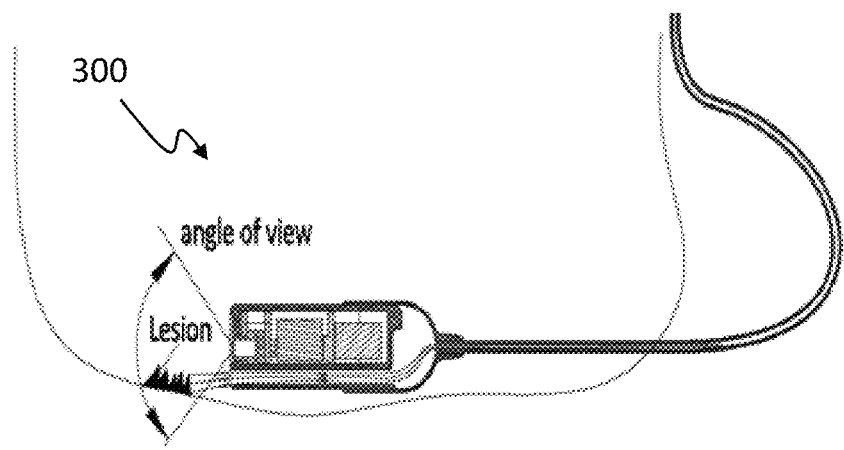
FIG. 4B is an illustrative schematic depicting a method for performing drug delivery using the capsule endoscope depicted in FIGS. 2A-2C.

Exemplary uses of the system 300 are shown in FIGS. 4A and 4B. As shown in FIG. 4A, the system 300 may be advanced to an illustrative fluid environment (in pancreatic juice). The imaging system in the capsule endoscope may be used to observe patient fluid in the field of view of the imaging system, thereby confirming the presence of patient fluid adjacent the port 218. When presence of sufficient patient fluid is determined (e.g., submersion of the port 218 in the patient fluid is determined), a negative pressure provided by the pressure modulator 330 may be formed in the tether 320, the channel, and the port 218. This negative pressure causes the patient fluid to be drawn into the port 218, the channel in the capsule endoscope, the tether 320, and out of the patient into a collection (e.g., syringe).

Additionally, as shown in FIG. 4B, the system 300 may be advanced to a region of interest including a lesion. The imaging system in the capsule endoscope may be used to observe the lesion in the field of view of the imaging system, thereby confirming that the port 218 is sufficiently near the lesion (e.g., the capsule endoscope is in a suitable treatment location and/or orientation). When the treatment location and/or orientation of the capsule endoscope is determined, a drug (e.g., therapeutic agent) may be delivered into the tether 320, and a positive pressure provided by the pressure modulator 330 may be formed in the tether 320, the channel, and the port 218. This positive pressure causes the drug to be urged down the tether, the channel, and the port 218 towards the lesion.

FIGS. 5A-5C depict another exemplary variation of a capsule endoscope 500 including a port 518 at a distal end of the capsule endoscope 500. Except as described below, the capsule endoscope 500 may be similar to the capsule endoscope 200 described above with reference to FIGS. 2A-2D, 3, and 4A-4B, where the endoscope components of the capsule endoscope 500 may be similar to like-numbered endoscope components of the capsule endoscope 200. However, in contrast to the flat distal cover 212 in the capsule endoscope 200, the capsule endoscope 500 may include a transparent domed or bulbous distal cover 512. The domed or bulbous distal cover 512 may, for example, enforce a minimum viewing distance between the lens of the imaging system and the region of interest. By providing a minimum distance along the optical axis of the imaging system between the lens and one or more objects to be viewed, the capsule endoscope may help ensure that the field of view is consistently sufficiently large.

Figure 6A:
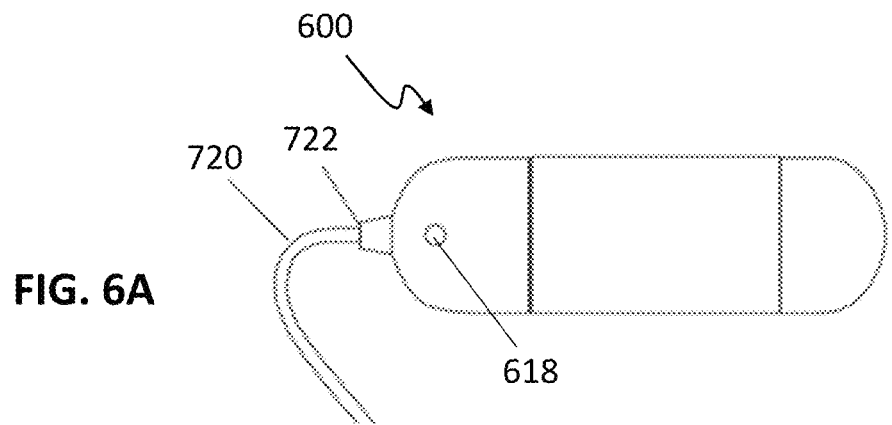
FIGS. 6A-6C are side, partial longitudinal cross-sectional, and longitudinal cross-sectional schematic views, respectively, of an exemplary variation of a capsule endoscope with a port at its proximal portion.
Figure 6B:
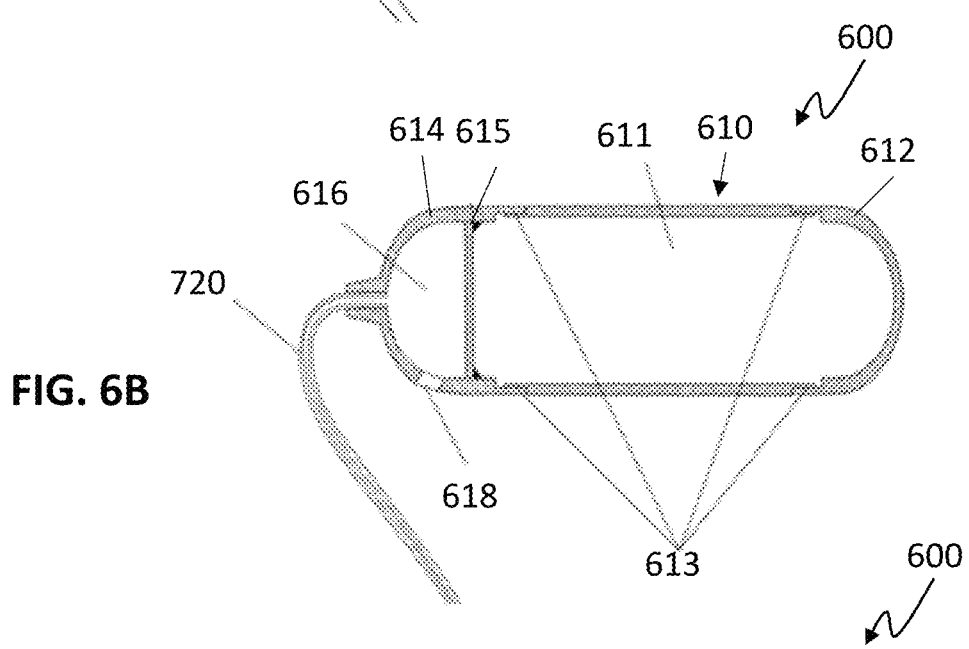
Figure 6C:
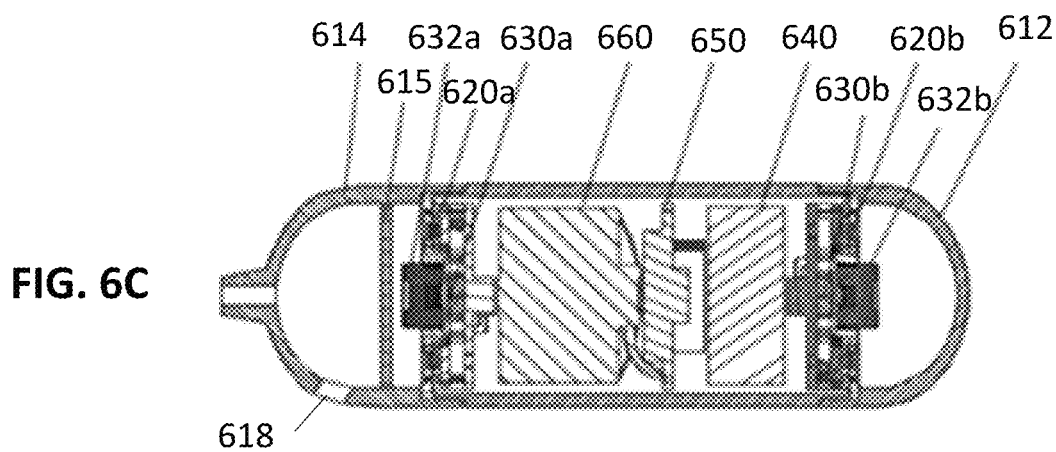

FIGS. 6A-6C depict another exemplary variation of a capsule endoscope 600 including a port 618 at a proximal end of the capsule endoscope 600. Except as described below, the capsule endoscope 600 may be similar to the capsule endoscope 200 described above with reference to FIGS. 2A-2D, 3, and 4A-4B, where the endoscope components of the capsule endoscope 600 may be similar to like-numbered endoscope components of the capsule endoscope 200.

The housing 610 of the capsule endoscope 600 may include a proximal cover 614 and a distal cover 612 coupled to a generally cylindrical structure as shown in FIG. 6B with a fluid-tight seal. The fluid-tight seal may, for example, be formed through the application of epoxy 613 or other adhesive around the adjoining surfaces of the covers and the cylindrical structure. Furthermore, the housing 610 may define an electronics compartment 611 that contains the endoscope components shown in FIG. 6C. The electronics compartment 611 may, for example, be bounded by the generally cylindrical structure and the distal cover 612, as well as an optically transparent proximal wall 615.

Unlike the capsule endoscope 200, the capsule endoscope 600 may include multiple imaging systems and multiple illumination systems. For example, as shown in FIG. 6C, the capsule endoscope 600 may include a proximal imaging system 630a and a proximal illumination system 620a that are arranged at a proximal end of the capsule endoscope 600 to view and illuminate a field of view adjacent to the proximal end of the capsule endoscope 600. The capsule endoscope 600 may additionally include a distal imaging system 630b and a distal illumination system 620b that are arranged at a distal end of the capsule endoscope 600 to view and illuminate a field of view adjacent to the distal end of the capsule endoscope 600. Although two imaging systems are depicted in the variation shown in FIG. 6C, it should be understood that in some variations only one imaging system may be included in the capsule endoscope 600 (e.g., at the proximal end of the capsule endoscope 600, near the port 618).

Furthermore, unlike the capsule endoscope 200, the capsule endoscope 600 may include a compartment 616 including a chamber as shown in FIGS. 6B and 6C. The chamber may be located in a proximal portion of the capsule endoscope. Like the compartment 216 described above, the compartment 616 may be in fluidic communication between a lumen in the tether 720 and the port 618, so as to provide a conduit for liquid biopsy and/or drug delivery. The compartment 616 may include a chamber, where a sidewall or other surface of the chamber may define the port 618. As shown in FIG. 6B, in some variations the chamber may be bound at least in part by the transparent proximal wall 615 and the proximal cover 614.

Figure 7:
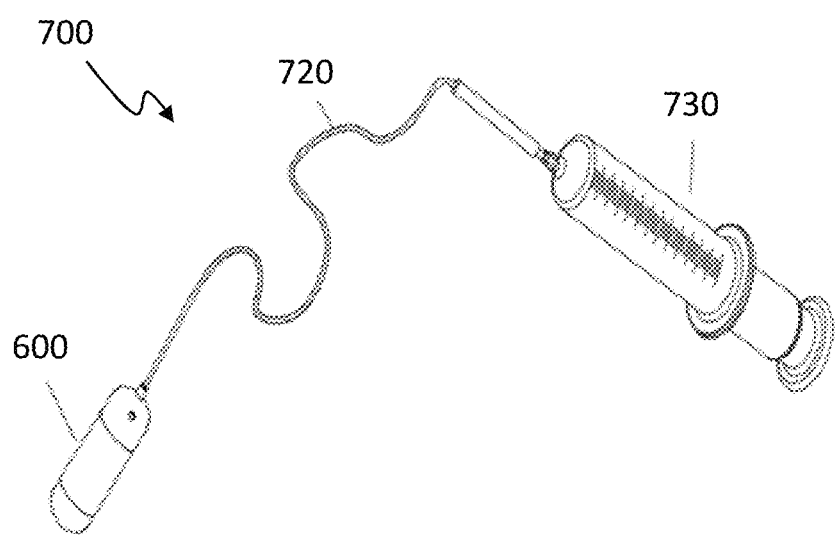
FIG. 7 is an illustrative schematic depicting an exemplary tethered system including the capsule endoscope variation depicted in FIGS. 6A-6C.

As shown in FIG. 7, in a system 700, the capsule endoscope 600 may be coupled to a tether 720 including a flexible member having a lumen, and the tether 720 may be coupled to a pressure modulator 730 (e.g., pressure source or vacuum source, such as a syringe or pump). The tether 720 may include a lumen, such as in a flexible member, and may be coupled to the capsule endoscope 600 in any suitable manner such as directly (e.g., with epoxy 722 as shown in FIG. 6A, with a barb fitting or other fitting) or via a clamp, as described in further detail below.

Figure 8A:
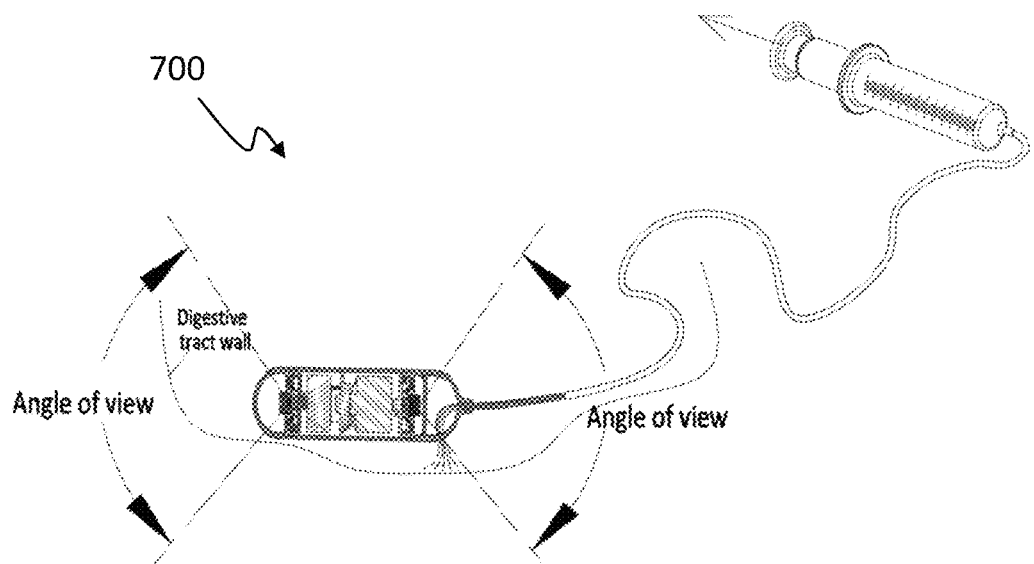
FIG. 8A is an illustrative schematic depicting a method for performing liquid biopsy using the capsule endoscope variation depicted in FIGS. 6A-6C.
Figure 8B:
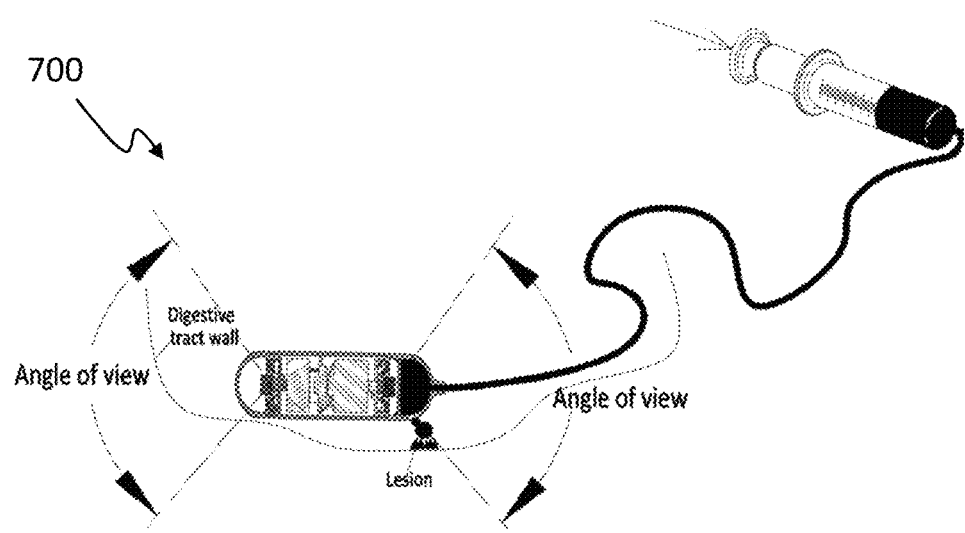
FIG. 8B is an illustrative schematic depicting a method for performing drug delivery using the capsule endoscope variation depicted in FIGS. 6A-6C.

Exemplary uses of the system 700 are shown in FIGS. 8A and 8B. As shown in FIG. 8A, the system 700 may be advanced to an illustrative fluid environment (e.g., in pancreatic juice). One or more imaging systems in the capsule endoscope may be used to help navigate the capsule endoscope to the region of interest and/or may be used to observe patient fluid. For example, a distal (front) imaging system may be primarily used to help position and/or orient the capsule endoscope to and near the region of interest, while a proximal (rear) imaging system near the port 618 may be used to assess the position of the port 618 relative to any patient fluid (and assess the presence of sufficient patient fluid). As another example, in variations in which the capsule endoscope has only a proximal imaging system near a proximal port 618, the proximal imaging system may be used to help general positioning and/or orientating of the capsule endoscope to the region of interest, as well as assess the position of the port relative to any patient fluid and assess the presence of sufficient patient fluid. When presence of sufficient patient fluid is determined (e.g., submersion of the port in the patient fluid is determined), a negative pressure provided by the pressure modulator 730 may be formed in the tether 720, the compartment 616, and the port 618. This negative pressure causes the patient fluid to be drawn into the port 618, the compartment 616 in the capsule endoscope, the tether 720, and out of the patient into a collection (e.g., syringe).

Additionally, as shown in FIG. 8B, the system 700 may be advanced to a region of interest including a lesion. Similarly to that described above with reference to FIG. 8A, one or more imaging systems in the capsule endoscope may be used to help navigate the capsule endoscope to the region of interest and/or may be used to observe a region of interest (e.g., lesion). In other words, the one or more imaging systems may be used to help confirm when the port 618 is proximate a region of interest for treatment (e.g., the capsule endoscope is in a suitable treatment location and/or orientation). When the treatment location and/or orientation of the capsule endoscope is determined, a drug (e.g., therapeutic agent) may be delivered into the tether 720, and a positive pressure provided by the pressure modulator 730 may be formed in the tether 720, the compartment 616, and the port 618. This positive pressure causes the drug to be urged down the tether, the compartment 616, and the port 618 towards the lesion.

Figure 9:
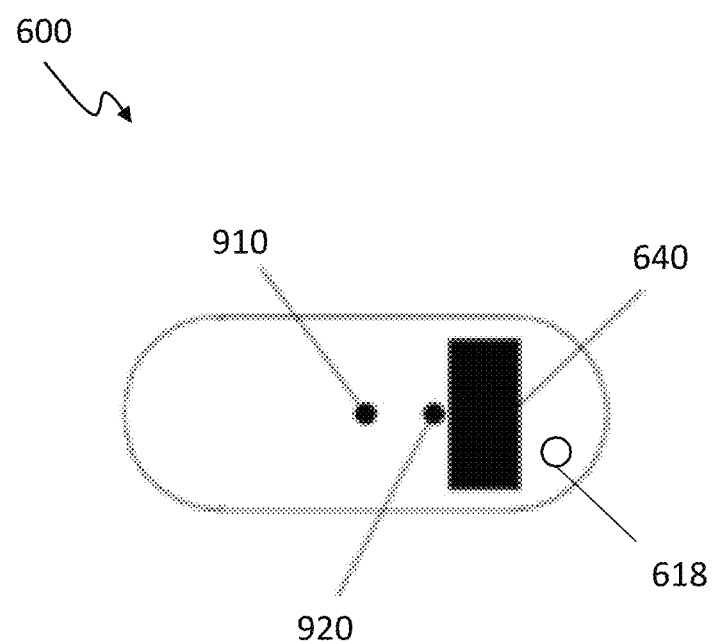
FIG. 9 is an illustrative schematic depicting an exemplary variation of a capsule endoscope having a biased center of gravity.

In some variations, as shown in FIG. 9, the capsule endoscope 600 may have a center of gravity 920 that is biased toward the proximal end of the capsule endoscope, such that the gravity may tend to help the submersion of the port 618 (located at the proximal portion of the capsule endoscope) in pooled fluid for obtaining liquid biopsy. As shown in FIG. 9, the center of gravity 920 may be axially offset from the centroid 910 (toward the proximal end of the capsule endoscope 600). The center of gravity may be adjusted appropriately by, for example, distributing more weight (e.g., magnet 640, which may be relatively dense) toward the proximal end of the capsule endoscope 600. However, the center of gravity may additionally or alternatively be adjusted in other suitable ways, such as a non-uniform distribution of housing material (e.g., thickness of the housing may be greater, or the housing may have a heavier material at a proximal end). Additionally or alternatively, a relatively buoyant element or feature (e.g., an air-containing compartment) may be located on an opposing end of the capsule endoscope relative to the port 618.

Tether

Generally, the tether functions to help retain the capsule endoscope in a desired region of interest (e.g., avoid reduced dwell times in the esophagus due to peristalsis, etc.) and provide a conduit for carrying a fluid from and/or to the capsule endoscope, such as a liquid biopsy from the capsule endoscope or a drug to the capsule endoscope. As described above, a proximal portion of the tether may extend to outside the patient and may be coupled to a pressure modulator (e.g.

pressure source or vacuum source) to control fluid flow through tether through positive pressure or negative pressure. The proximal portion of the tether may further be coupled to a collection unit (e.g., syringe, other container) for collecting fluid withdrawn from the patient through the tether, and/or to a drug source (e.g., syringe, other container) for delivering into the patient through the tether. In some variations, the proximal portion may be branched and include one end coupled to a vacuum source (and/or a drug source) and another end coupled to a pressure source (and/or a collection unit). In some of these variations, one or more valves or other fluidic control system to switch between introducing a negative pressure and a positive pressure in the tether.

The tether may be removably coupled to the capsule endoscope. For example, the tether may be coupled to the capsule endoscope so as to follow the capsule endoscope (e.g., down a patient's gastrointestinal tract) as the capsule endoscope is advanced in the patient. Furthermore, the tether may be uncoupled from the capsule endoscope to allow the capsule endoscope to pass through the patient (e.g., naturally, such as through peristalsis) and then withdrawn from the patient. In some variations, a port for taking a liquid biopsy and/or delivering a drug may be located on a portion of the tether. Alternatively, the tether may be withdrawn from the patient, with the capsule endoscope remaining coupled to the tether, in order to remove the capsule endoscope from the patient.

Figures 10A, 10B:
FIG. 10A is an illustrative schematic depicting a flexible member in an exemplary variation of a tether.
FIG. 10B is an illustrative schematic depicting exemplary dimension ranges of a flexible member of a tether.

As shown in FIGS. 10A and 10B, in some variations a tether 1000 may include a flexible member having a lumen 1010. Generally, the flexible member may be an elongated tubular member configured to be advanced safely and comfortably into a patient's body cavity. In some variations, the flexible member may be between about 2 mm to about 10 mm in length, or 9 mm in length. The flexible member may include a soft, flexible material such as silicone elastomer (e.g., having a Shore A hardness of between about 35 and about 65, or about 50). Furthermore, in an exemplary variation the flexible member may have an inner diameter of about 0.5 mm (between about 0.4 mm and about 0.6 mm, for example), and an outer diameter of about 1 mm (between about 0.9 mm and about 1.3 mm, for example), with a wall thickness of about 0.25 mm. However, in other variations the flexible member may include other combinations of length, material types and/or dimensions.

Various exemplary variations of the tether having different arrangements of tether components are described in further detail below.

FIGS. 11A-11D depict an exemplary variation of a tether 1120 including a flexible member 1122 and a clamp 1124 for coupling the flexible member 1122 to a capsule endoscope, where the clamp 1124 includes a port 1128 in fluidic communication with a lumen of the flexible member 1122. Furthermore, the clamp 1124 may be suitable for a "double lens" capsule endoscope having both a proximal imaging system on a proximal end of the capsule endoscope, and a distal imaging system on a distal end of the capsule endoscope.

Figure 11A:
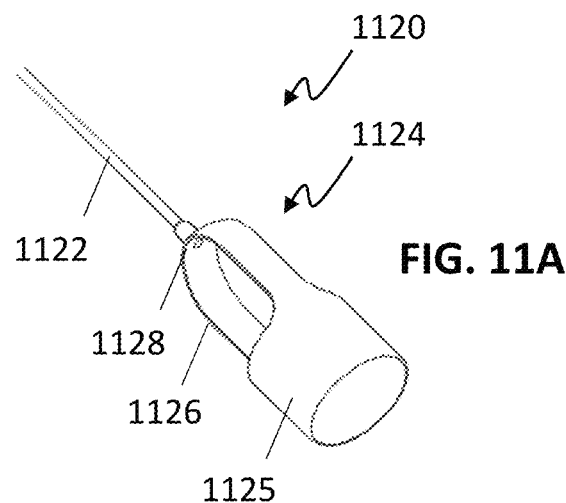
FIG. 11A is an illustrative schematic depicting an exemplary variation of a tether with a clamp having a port.
Figure 11B:
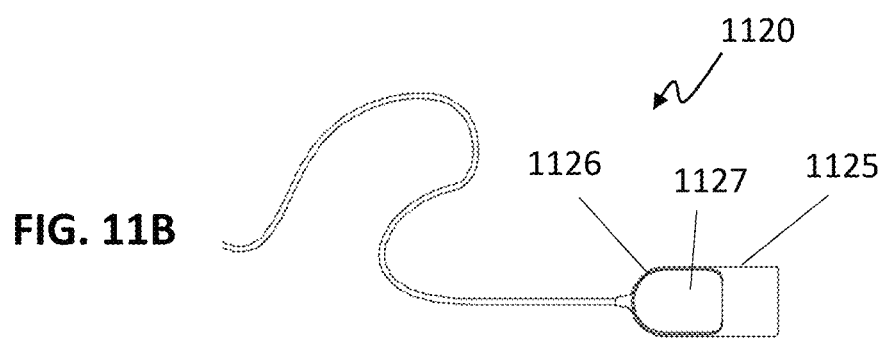
FIG. 11B is an illustrative schematic depicting a side view of the exemplary tether variation depicted in FIG. 11A.
Figure 11C:
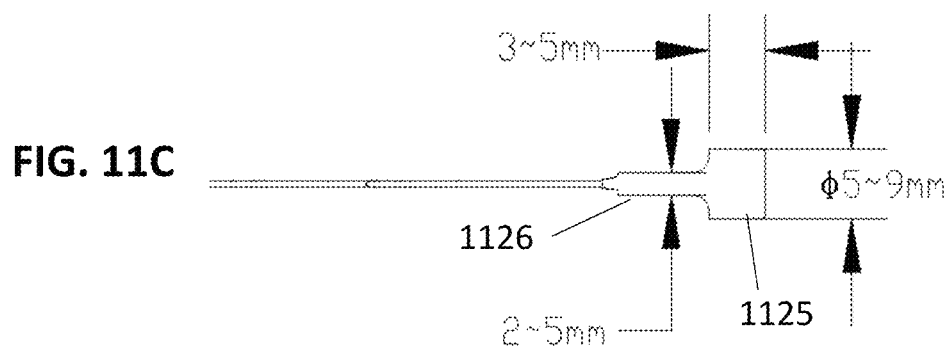
FIG. 11C is an illustrative schematic depicting exemplary dimension ranges of the exemplary tether variation depicted in FIG. 11A.
Figure 11D:
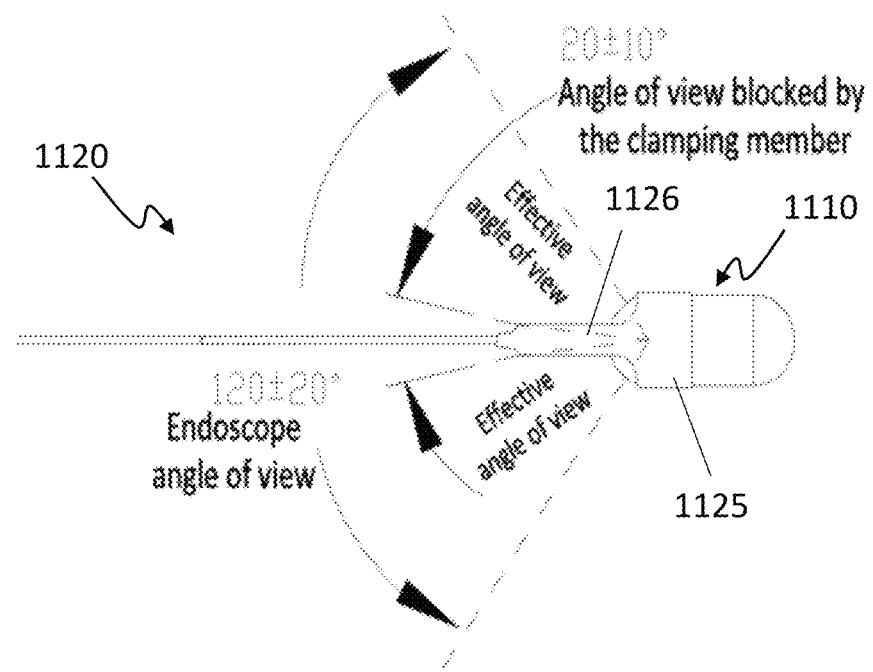
FIG. 11D is an illustrative schematic depicting ranges of field of view in a system incorporating the exemplary tether variation depicted in FIG. 11A.

As shown in FIG. 11D, the clamp 1124 may include a sheath 1125 that is configured to at least partially surround and attach to at least a portion of the capsule endoscope 1110, thereby coupling the tether 1120 to the capsule endoscope 1110. The sheath 1125 may include open proximal and distal ends, where the open proximal end forms a window providing visual clearance (i.e., does not significantly obstruct) a proximal imaging system on the proximal end of the capsule endoscope. As shown in FIG. 11A, the sheath 1125 may surround an entire circumference of a proximal portion of the capsule endoscope 1110. However, in other variations the sheath may not surround an entire circumference; for example, the sheath may have a "C"-shaped cross-sectional shape.

The clamp may further include an anchor member 1126 configured to couple the clamp to the flexible member. The anchor member 1126 may be integrally formed with the sheath 1125 or formed separately and coupled to the sheath 1125 with one or more suitable fasteners and/or mechanical fittings, etc. Furthermore, the anchor member 1126 may be coupled to a distal end of the flexible member 1122, such as by a mechanical fitting and/or epoxy. Alternatively, the anchor member 1126 may be integrally formed with a distal end of the flexible member 1112, such as through an injection molding process or the like.

As shown in FIG. 11B, the anchor member 1126 may be generally arcuately shaped (e.g., "C"-shaped or "U"-shaped) to enable coupling of the clamp and the flexible member at a location that is offset from the capsule endoscope, so as to not significantly block the field of view of the proximal imaging system of the capsule endoscope. For example, as shown in FIG. 11B, the anchor member 1126 may provide a window region 1127 that, together with the open proximal end of the sheath 1125, may allow for a substantial portion of the field of view of the proximal imaging system to remain unobscured. Furthermore, as shown in FIG. 11C, the side profile of the anchor member 1126 may be smaller than the diameter of the sheath 1125. Overall, as shown in FIG. 11D, the clamp 1124 may provide for an effective (unobscured) field of view of the proximal imaging system that is not significantly smaller or narrower than the field of view without the clamp 1124 attached. For example, FIG. 11C illustrates exemplary dimensions for the clamp 1124, including a sheath diameter of between about 5 mm and about 9 mm, a sheath length between about 3 mm and about 5 mm, and an anchor member width of between about 2 mm and 5 mm. As shown in FIG. 11D, when combined with a clamp 1124 of these dimension ranges, an endoscope field of view having an angle of view of about 120 degrees (e.g., between about 100 degrees and about 140 degrees) may only be reduced by about 20 degrees (e.g., between about 10 degrees and about 30 degrees). Thus, the resulting effective field of view remains substantially unobscured by the clamp 1124.

In some variations, the anchor member 1126 may include a single component forming an arcuate structure that extends across an opening of the sheath (i.e., arcuate segments that are integrally formed). However, alternatively, the anchor member may include multiple components each forming a separate segment of such an arcuate structure. For example, in some variations, the anchor member 1126 may include two or more separate arcuate segments that connect end-to-end (or longitudinally overlap) to form a single arcuate structure similar to the anchor member 1126 shown in FIG. 11A. For example, an anchor member 1126 may include two opposing arcuate segments that extend from opposite sides of a proximal end of the sheath 1125 towards the apex of the anchor member 1126. These two opposing arcuate segments may be of approximately equal length and meet at the apex of the anchor member 1126 (e.g., near the port 1128), or may be of unequal length and meet on either side of the anchor member 1126.

Figure 11E:
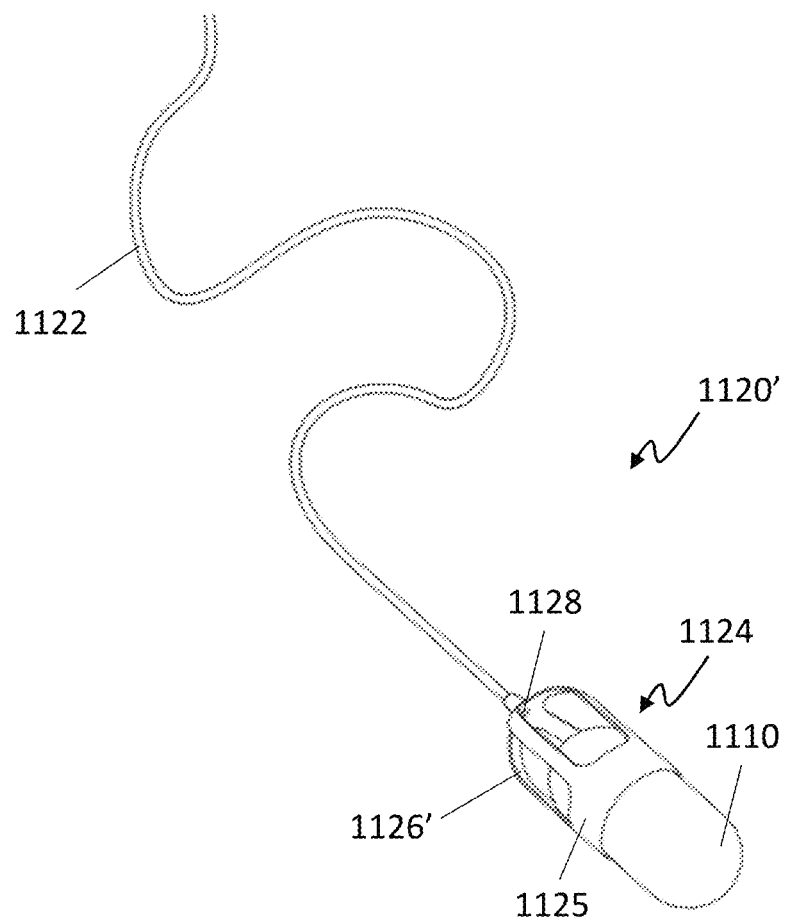
FIG. 11E is an illustrative schematic depicting an exemplary variation of a tether with a clamp having an anchor member with multiple arcuate structures.

Furthermore, in some variations, the anchor member may include multiple arcuate structures oriented in different planes (e.g., forming a dome shape with multiple window regions). For example, FIG. 11E depicts a tether 1120' including an anchor member 1126' having four arcuate segments that are oriented in orthogonal planes (i.e., arcuate segments distributed approximately 90 degrees circumferentially around the anchor member 1126' and the sheath 1125) and form multiple window regions. The arcuate segments may be equally distributed around the anchor member 1126' and the sheath 1125 (e.g., such that the anchor member 1126' is generally radially symmetrical), or alternatively may be unequally distributed. In some variations, additional arcuate segments may, for example, improve structural integrity of the anchor member (e.g., multi-directional and/or torsional rigidity). Furthermore, additional arcuate segments distributed around the anchor member 1126' and the sheath 1125 (e.g., when equally distributed) may help improve balance of forces when the tether is attached to and interacting with (e.g., pulling) the capsule endoscope. It should be understood that other variations of the tether similar to tethers 1120 and 1120' may include any suitable number of arcuate segments (e.g., 3, 5 or more, etc.). The width of the arcuate segments may decrease with increasing numbers of arcuate segments, so as to maintain a sufficiently unobscured field of view for the capsule endoscope imaging system.

The anchor member 1126 may further include a port 1128 in fluidic communication with the lumen of the flexible member. The port 1128 may be an opening that is configured to be axially offset from the proximal portion of the capsule endoscope, such as opposite the proximal imaging system, such that the proximal imaging system may view the environment around the port 1128 (e.g., to confirm the presence of sufficient patient fluid near the port 1128 for withdrawal of patient fluid through the port, to confirm location of a region of interest relative to the port 1128 for receiving a drug through the port, etc.).

Figure 12:
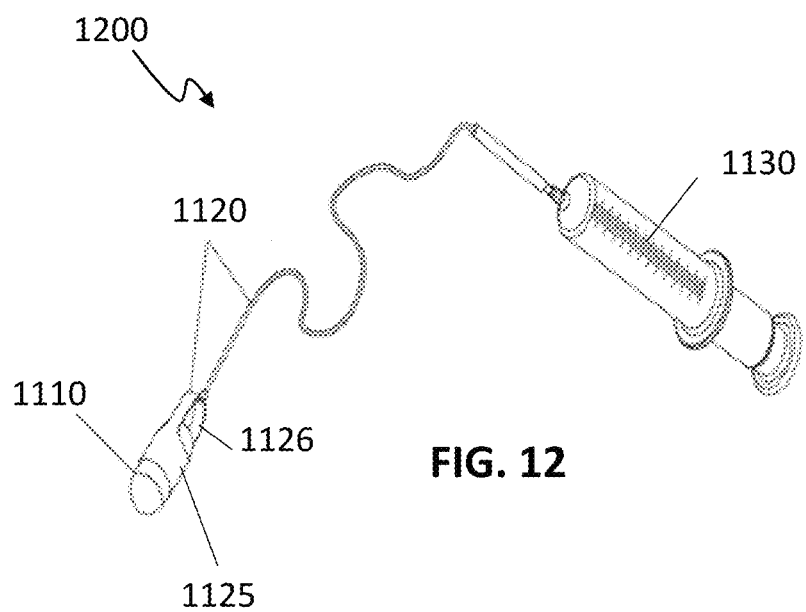
FIG. 12 is an illustrative schematic depicting an exemplary variation of a tethered system including the tether variation depicted in FIG. 11A.

For example, as shown in FIG. 12, in a system 1200, the capsule endoscope 1110 may be coupled to a tether 1120 via a clamp 1125. The capsule endoscope 1110 may, for example, be similar to the capsule endoscope 600 described above with reference to FIGS. 6A-6C having proximal and distal imaging systems, except that the capsule endoscope 1110 may omit a port. The tether 1120 may be coupled to a pressure modulator 1130 (e.g., pressure source or vacuum source, such as a syringe or pump). The tether 1120 may include a lumen, such as in a flexible member, and the clamp 1125 may include a port in fluidic communication with the lumen.

Figure 13A:
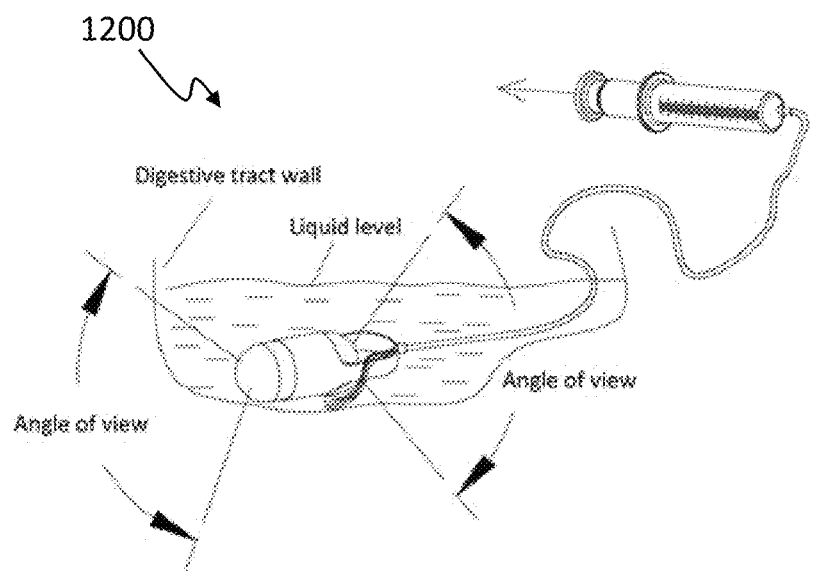
FIG. 13A is an illustrative schematic depicting a method for performing liquid biopsy using the tether variation depicted in FIG. 11A.
Figure 13B:
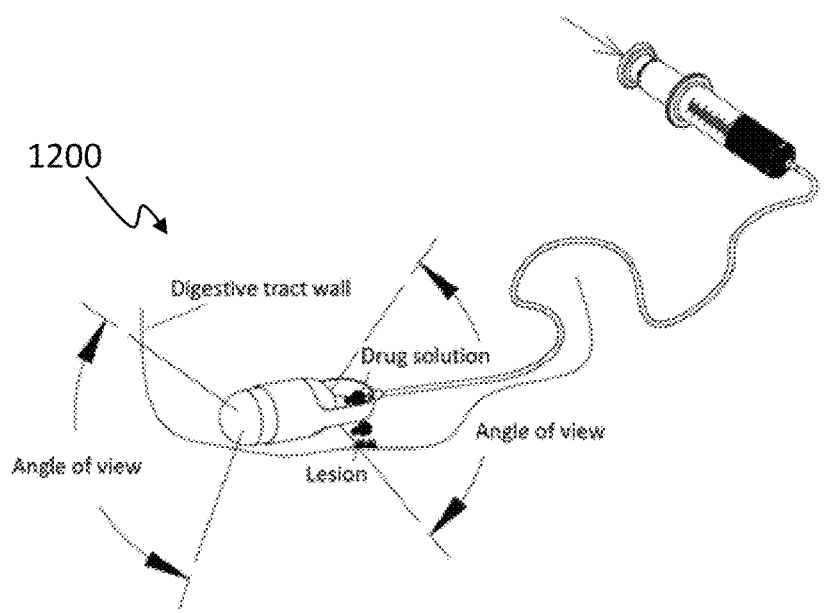
FIG. 13B is an illustrative schematic depicting a method for performing drug delivery using the tether variation depicted in FIG. 11A.

Exemplary uses of the system 1200 are shown in FIGS. 13A and 13B. As shown in FIG. 13A, the system 1200 may be advanced to an illustrative fluid environment (e.g., in pancreatic juice). The distal imaging system and/or proximal imaging system in the capsule endoscope may be used to observe patient fluid in the surroundings of the capsule endoscope, thereby confirming the presence of patient fluid adjacent the port 1128. When presence of sufficient patient fluid is determined (e.g., submersion of the port 1128 in the patient fluid is determined), a negative pressure provided by the pressure modulator 1130 may be formed in the tether 1120 and in the port 1128. This negative pressure causes the patient fluid to be drawn into the port 1128, the tether 1120, and out of the patient into a collection (e.g., syringe).

Additionally, as shown in FIG. 13B, the system 1200 may be advanced to a region of interest including a lesion. The distal imaging system and/or proximal imaging system in the capsule endoscope may be used to observe the lesion, thereby confirming that the port 1128 is sufficiently near the lesion (e.g., the capsule endoscope is in a suitable treatment location and/or orientation). When the treatment location and/or orientation of the capsule endoscope is determined, a drug (e.g., a therapeutic agent) may be delivered into the tether 1120, and a positive pressure provided by the pressure modulator 1130 may be formed in the tether 1120 and the port 1128. This positive pressure causes the drug to be urged down the tether and out of the port toward the lesion.

Figure 14A:
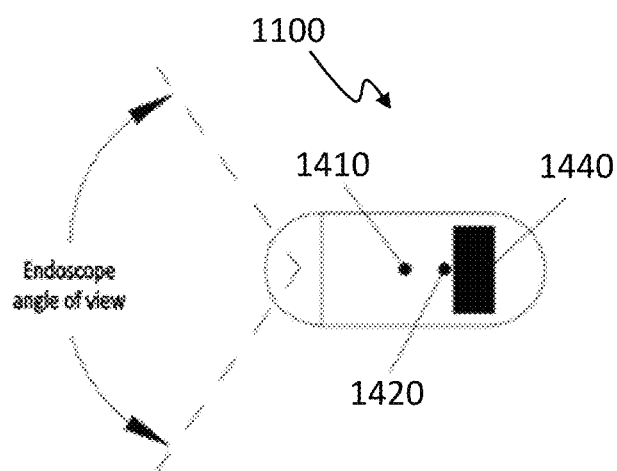
FIG. 14A is an illustrative schematic depicting an exemplary variation of a capsule endoscope having a biased center of gravity.
Figure 14B:
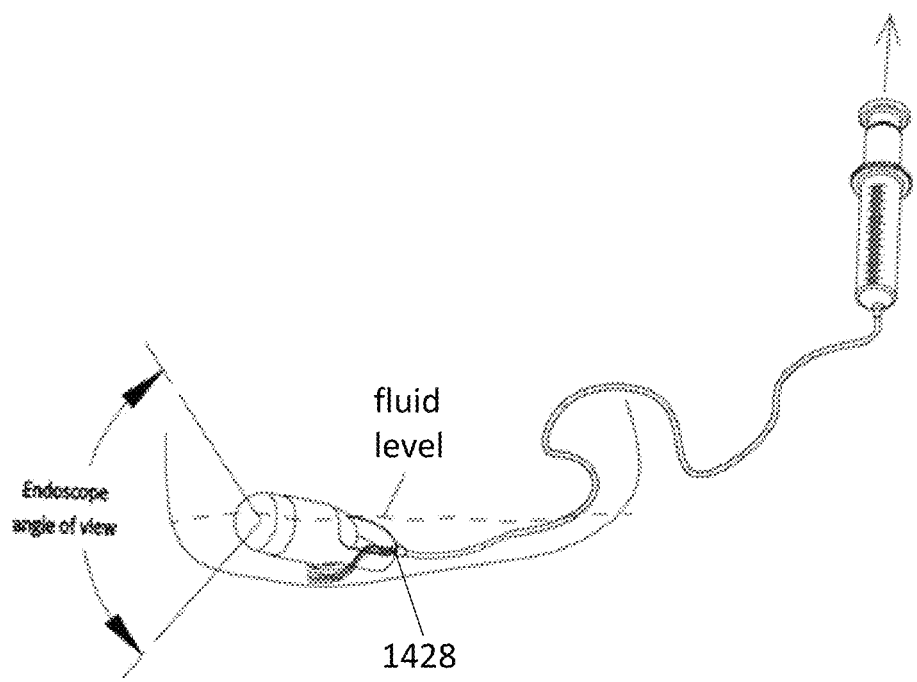
FIG. 14B is an illustrative schematic depicting the capsule endoscope variation depicted in FIG. 14A in combination with the tether variation depicted in FIG. 11A.

In some variations, as shown in FIGS. 14A and 14B, the capsule endoscope 1100 may have a center of gravity 1420 that is biased toward the proximal end of the capsule endoscope, such that the gravity may tend to help the submersion of the port 1428 (located in the tether coupled to a proximal end of the capsule endoscope 1110) in pooled fluid for obtaining liquid biopsy. As shown in FIG. 14A, the center of gravity 1420 may be axially offset from the centroid 1410 (toward the proximal end of the capsule endoscope 1100). The center of gravity may be adjusted appropriately by, for example, distributing more weight (e.g., magnet 1440, which may be relatively dense) toward the proximal end of the capsule endoscope 1100. However, the center of gravity may additionally or alternatively be adjusted in other suitable ways, such as a non-uniform distribution of housing material (e.g., thickness of the housing may be greater, or the housing may have a heavier material at a proximal end). Additionally or alternatively, a relatively buoyant element or feature (e.g., an air-containing compartment) may be located on an opposing end of the capsule endoscope relative to the port 1428.

Figure 15A:
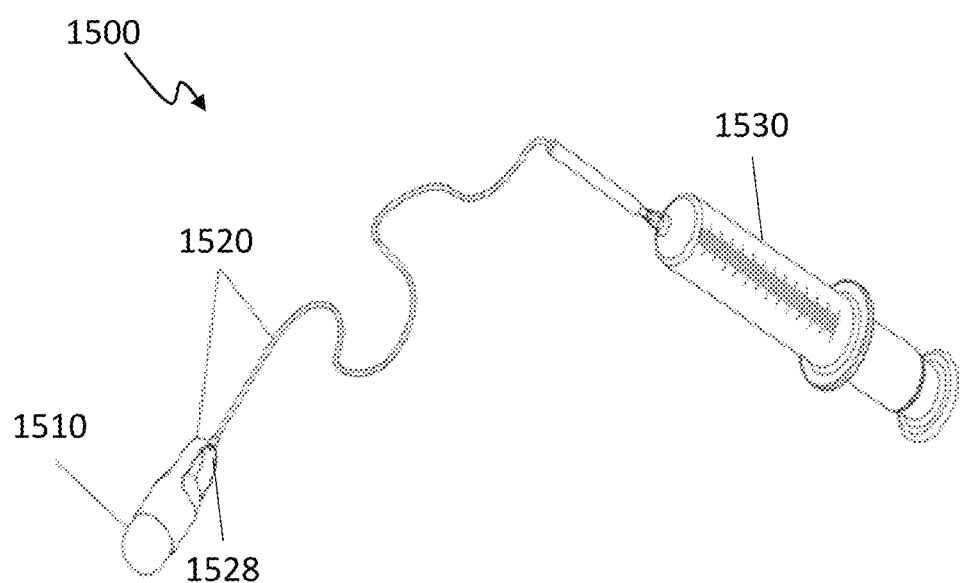
FIG. 15A is an illustrative schematic depicting another exemplary variation of a tethered system including the tether variation depicted in FIG. 11A.
Figure 15B:
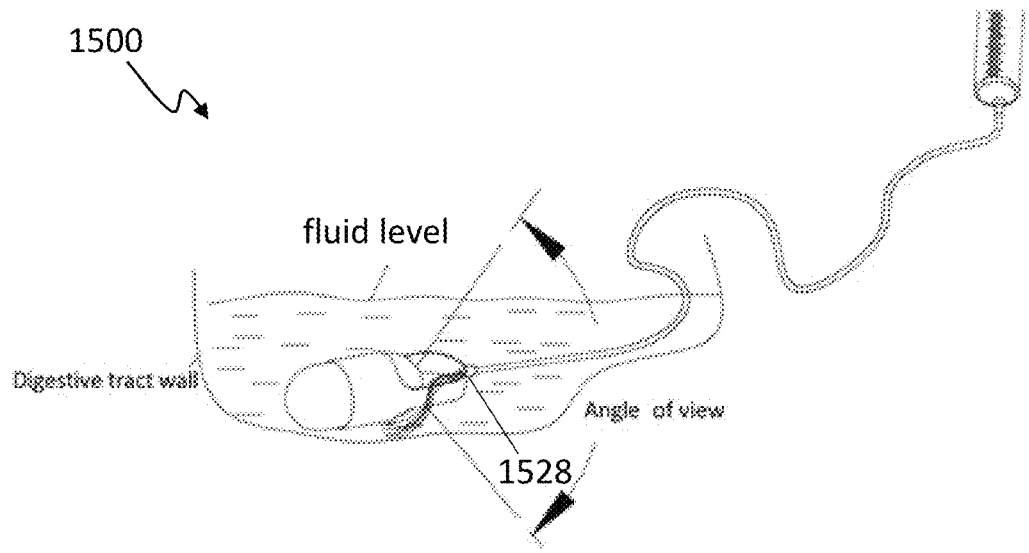
FIG. 15B is an illustrative schematic depicting a method for performing liquid biopsy using the tethered system variation depicted in FIG. 15A.
Figure 15C:
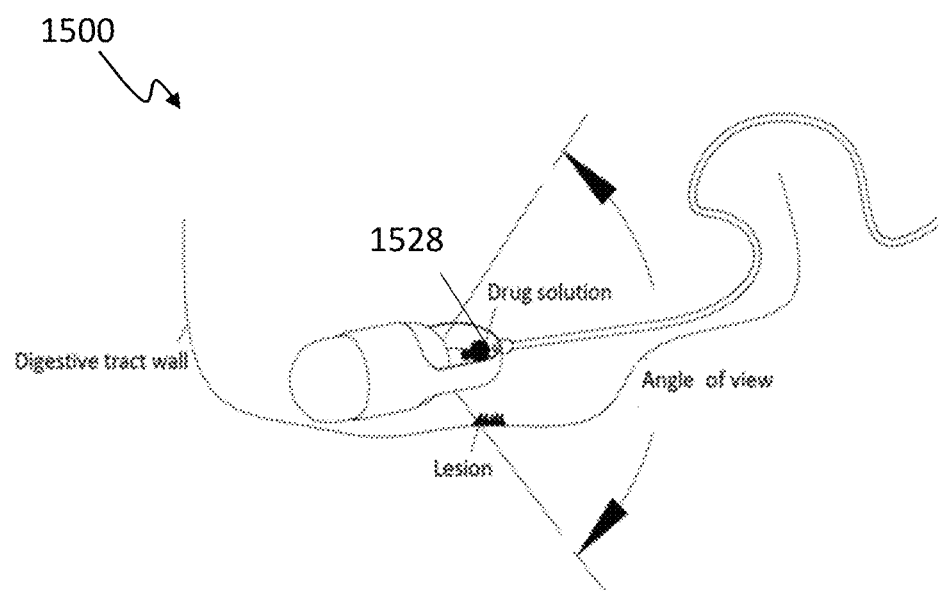
FIG. 15C is an illustrative schematic depicting a method for performing drug delivery using the tethered system variation depicted in FIG. 15A.

FIGS. 15A-15C depict a system 1500 including another exemplary variation of a tether 1520 including a flexible member and a clamp for coupling the flexible member to a capsule endoscope 1510, where the clamp includes a port 1528 in fluidic communication with a lumen of the flexible member. The system 1500 may be similar to the system 1200 described above with reference to FIGS. 12, 13A-13B, and 14A-14B, except as described below. In the system 1500, the clamp may be suitable for a "single lens" capsule endoscope having only a proximal imaging system on a proximal end of the capsule endoscope. As shown in FIG. 15B, the proximal imaging system in the capsule endoscope may have a field of view not substantially obscured by the clamp of the tether, including the surroundings of the port 1528. Accordingly, when presence of sufficient patient fluid is determined, a negative pressure provided by the pressure modulator 1530 may be formed in the tether 1520 and in the port 1528. This negative pressure causes the patient fluid to be drawn into the port 1528, the tether 1520, and out of the patient into a collection (e.g., syringe). Similarly, as shown in FIG. 15C, the proximal imaging system in the capsule endoscope may be used to determine whether the port 1528 is sufficiently near a lesion. When a treatment location and/or orientation of the capsule endoscope is determined, a drug may be delivered into the tether 1528, and a positive pressure provided by the pressure modulator 1530 may be formed in the tether 1520 and the port 1528. This positive pressure causes the drug to be urged down the tether and out of the port toward the lesion.

Figure 16A:
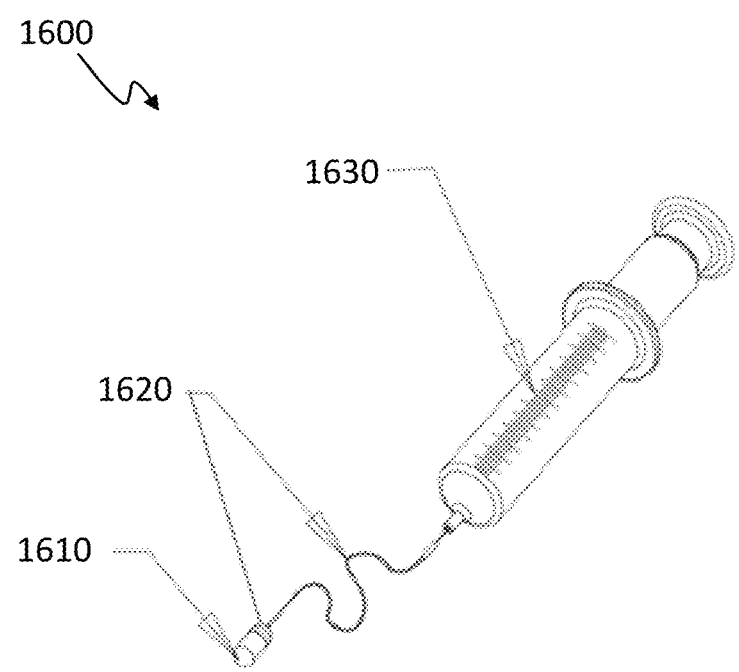
FIG. 16A is an illustrative schematic depicting another exemplary variation of a tethered system including a tether with a suction cup.
Figure 16B:
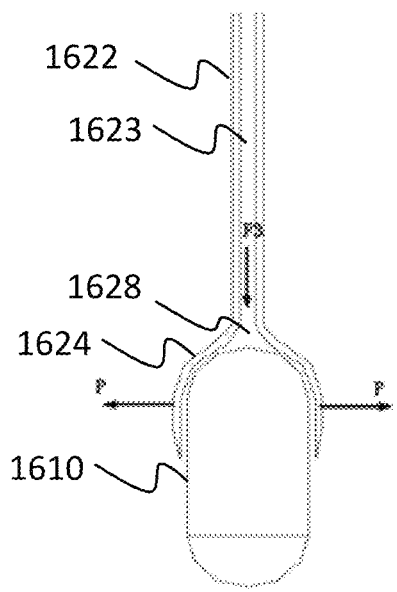
FIG. 16B is a force diagram illustrating disengagement between the capsule endoscope and the tether depicted in FIG. 16A.

As shown in FIGS. 16A and 16B, in some variations, a tether 1620 may include a port that is configured to permit passage of fluid therethrough after separation from the capsule endoscope. As shown in FIG. 16A, a tethered system 1600 may include a tether 1620 releasably coupled to a capsule endoscope 1610 and to a pressure modulator 1630 (e.g., syringe or pump). As shown in FIG. 16B, similar to the tether variations described above, the tether 1620 may include a flexible member 1622 having a lumen 1623. However, in this variation, the tether 1620 may include a port 1628 in fluidic communication with the lumen 1623 and which opens to a suction cup 1624 for receiving the capsule endoscope 1610. The suction cup 1624 may be soft and flexible, and may be formed, for example, out of the same or similar material as the flexible member 1622 (e.g., silicone). In some variations, the internal shape of the suction cup 1624 may be smooth and generally complementary (e.g., correspond) to the shape of the external housing of the capsule endoscope 1610.

Figure 16C:
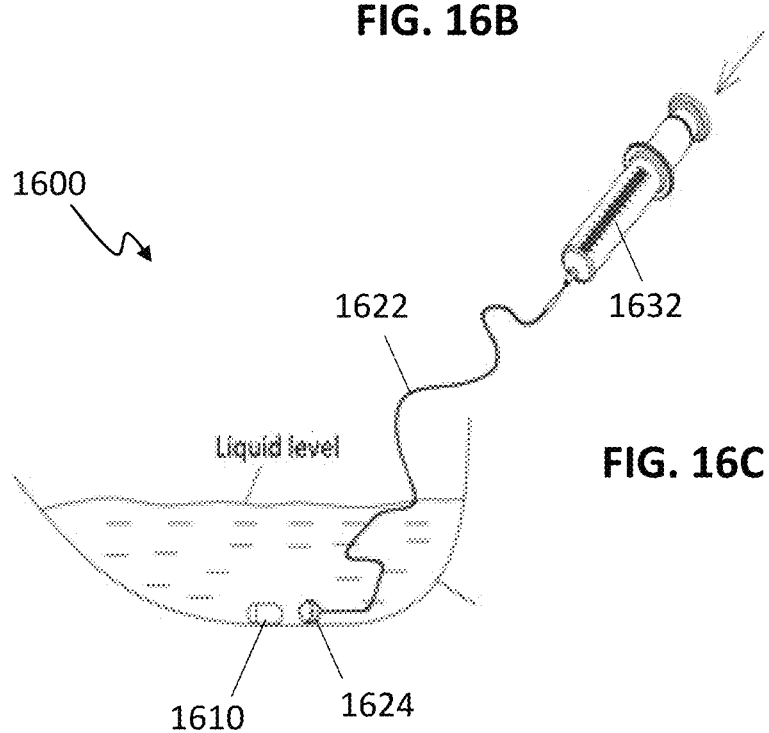
FIG. 16C is an illustrative schematic depicting disengagement of the capsule endoscope and the tether depicted in FIG. 16A.

Generally, a vacuum state within the lumen 1623 retains the capsule endoscope 1610 within the suction cup 1624. As shown in FIG. 16B, pressurization within the lumen 1623 (e.g., inflation via a coupled pressure source), the suction cup 1624 may expand radially outward as shown by the arrows P, and/or an axial pushing force F3 may provide thrust against the capsule endoscope 1610, thereby releasing the capsule endoscope 1610 from the suction cup 1624. FIG. 16C illustrates an exemplary method of decoupling the capsule endoscope 1610 from the suction cup 1624. In this variation, a conduit may extend from a pressure source (syringe 1632), through a lumen of the flexible member 1622, and through a port leading to a suction cup 1624. When the pressure source provides positive pressure in the conduit (e.g., by depressing the plunger on syringe 1632), the expansion of the suction cup 1624 and/or the pushing force through the conduit may cause the suction cup 1624 to disengage, thereby releasing the capsule endoscope 1610. After the release of the capsule endoscope 1610, the port 1628 may be free to permit the exchange of fluid between the lumen of the flexible member 1622 and the environment in which the port 1628 is placed.

Figure 17A:
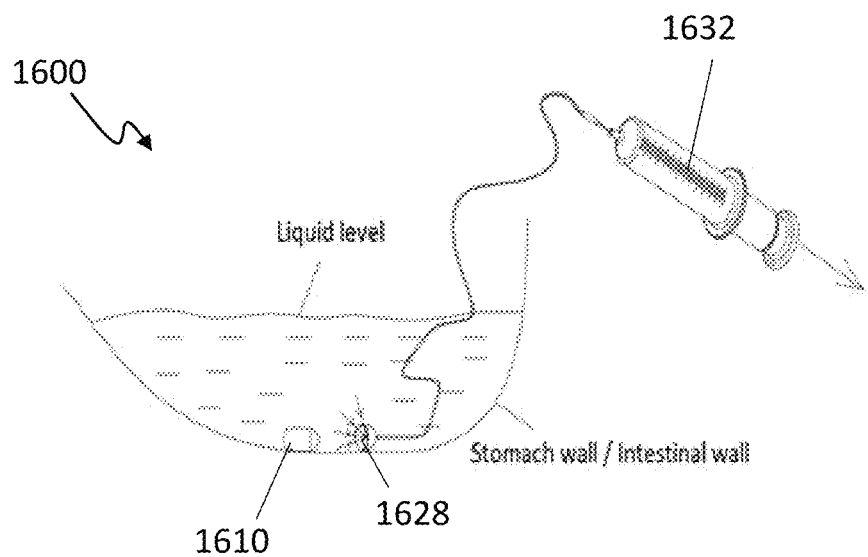
FIG. 17A is an illustrative schematic depicting a method for performing liquid biopsy using the tethered system variation depicted in FIG. 16A.

Such disengagement between the capsule endoscope and the tether may, for example, occur at a region of interest where it may be desirable to obtain a biopsy of patient fluid and/or deliver drugs through the port. As shown in FIG. 17A, the system 1600 may be advanced to an illustrative fluid environment (e.g., in pancreatic juice). One or more imaging systems in the capsule endoscope may be used to help navigate the capsule endoscope to the region of interest and/or may be used to observe patient fluid. When presence of sufficient patient fluid is determined, the capsule endoscope may be disengaged from the tether as described above. Thereafter, a negative pressure provided by the pressure modulator (e.g., syringe 1632) may be formed in the tether and the port 1628. This negative pressure causes the patient fluid to be drawn into the port 1628, into the tether, and out of the patient into a collection (e.g., syringe). Furthermore, the now-detached capsule endoscope 1610 may be controlled (e.g., via an external magnetic control system as described below) such that its imaging system(s) observe the biopsy process and enable confirmation that a sample was appropriately obtained.

Figure 17B:
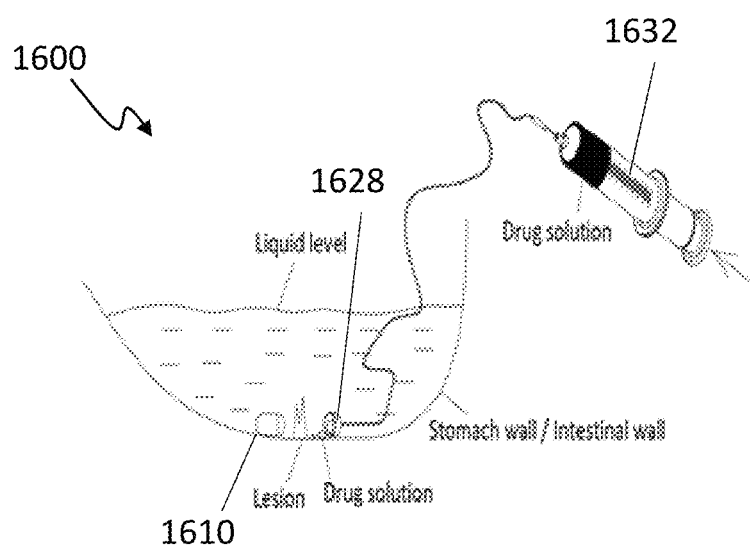
FIG. 17B is an illustrative schematic depicting a method for performing drug delivery using the tethered system variation depicted in FIG. 17A.

As another example, as shown in FIG. 17B, the system 1600 may be advanced to a region of interest including a lesion. Similarly to that described above, one or more imaging systems in the capsule endoscope may be used to help navigate the capsule endoscope. When the capsule endoscope has been navigated to the desired region of interest, the capsule endoscope may be disengaged from the tether as described above. Thereafter, a positive pressure provided by the pressure modulator (e.g., syringe 1632) may be formed in the tether and the port 1628. This positive pressure causes the drug to be urged down the tether and through the port 1628 towards the lesion. Furthermore, the now-detached capsule endoscope 1610 may be controlled (e.g., via an external magnetic control system as described below) such that its imaging system(s) observe the effect of drug delivery and enable confirmation that the drug was appropriately delivered.

FIGS. 18A-18C depict another exemplary variation of a tether 1820 for coupling to a capsule endoscope, where the tether 1820 includes a housing having a port permitting passage of fluid therethrough. The tether 1820 includes a clamp including a flexible, elastic sheath 1824 for releasably engaging a capsule endoscope, and a housing 1826 including a chamber between the sheath 1824 and a flexible member 1822. For example, the sheath 1824 may be coupled to the housing 1826 through adjoining circumferential surfaces 1825 (e.g., via mechanical interfit, epoxy, etc) or any suitable feature. Furthermore, the housing 1826 may be coupled to the flexible member 1822 through adjoining circumferential surfaces 1827 (e.g., via mechanical interfit, epoxy, etc.) or any suitable feature. FIG. 18C illustrates exemplary dimensional ranges for the sheath 1824, which may have a length of between about 5 mm and 10 mm, an outer diameter between about 5 mm and about 9 mm, and a wall thickness between about 0.05 mm and about 0.5 mm.

As shown in FIGS. 18A and 18B, the housing 1826 may furthermore include a port 1828. The port 1828 may be selectively covered by a valve 1830 to modulate flow through the port 1828. In some variations, the valve 1830 may be a one-way valve that permits flow only in one direction. Additionally or alternatively, the valve 1830 may be biased towards a closed state, such as with a spring 1832 (e.g., torsion spring, flexible member functioning similar to a spring, and the like). Exemplary operation of the port 1828 and valve 1830 is described in further detail below.

Figure 19A:
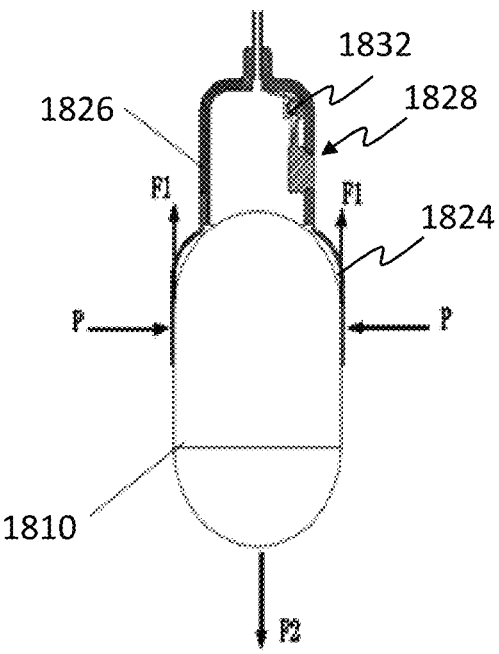
FIG. 19A is a force diagram illustrating engagement of the capsule endoscope with the tether variation depicted in FIGS. 18A and 18B.

In some variations, the sheath 1824 and the housing 1826 may cooperate to couple the capsule endoscope to the tether 1820. For example, as shown in FIG. 19A, the sheath 1824 may elastically deform to constrict around and engage the capsule endoscope 1810, thereby generating a pressure P that produces a friction force F1 on the contact surface between the sheath 1824 and the capsule endoscope 1810. The engagement between the capsule endoscope 1810 and the sheath 1824 may be substantially fluid-tight. Friction force F1 tends to retain the capsule endoscope 1810 within the sheath 1824. As shown in the diagram of FIG. 19A, a force F2 (countering the friction force F1) is produced by the sheath 1824 under environmental pressure (e.g., due to peristaltic pressure from the digestive tract muscles). As long as F1>F2, the capsule endoscope is retained in the sheath 1824.

Figure 19B:
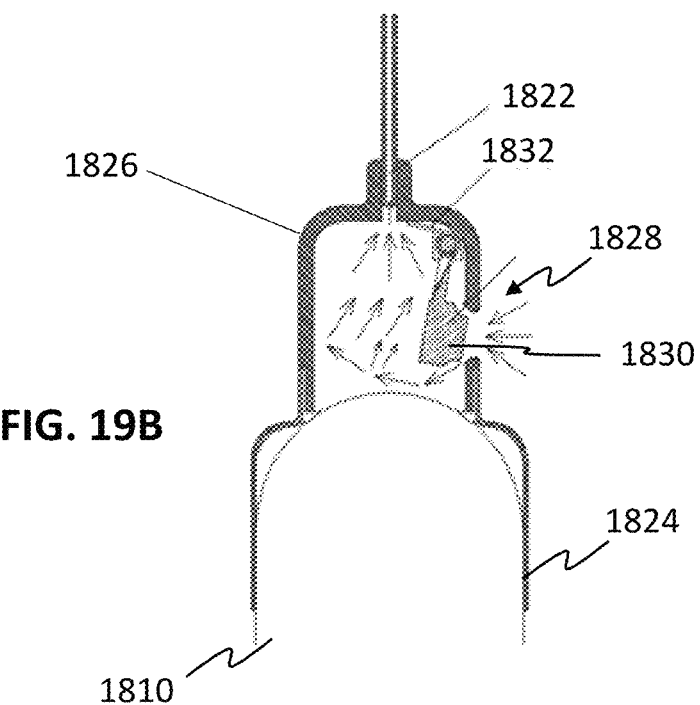
FIG. 19B is an illustrative schematic of opening of the port in the tether variation depicted in FIGS. 18A and 18B.

While the capsule endoscope 1810 is retained in the sheath 1824, controlled pressure differentials between inside of the housing 1826 and outside of the housing 1826 may open or close the valve 1830 covering the port 1828. For example, as shown in FIG. 19B, the chamber of the housing 1826 may be in fluidic communication with the lumen of the flexible member 1822, such that a vacuum source coupled to the flexible member 1822 may produce a sufficient pressure drop within the chamber in order to overcome the spring force biasing the valve 1830 closed. In other words, once the internal housing pressure is reduced to be lower than the pressure outside of the housing (by a differential sufficient to overcome the spring force), the valve 1830 may open, thereby permitting passage of fluid through the port 1828. In the open state shown in FIG. 19B, for example, fluid from outside the housing 1826 may enter the housing 1826, flow into the chamber, into the lumen of the flexible member 1822, and into a collection unit outside of the patient.

For example, in a method for obtaining a liquid biopsy, the capsule endoscope 1810 may be advanced to a region of interest, and an imaging system of the capsule endoscope may be used to observe surrounding patient fluid. When presence of sufficient patient fluid is determined, a sufficient negative pressure may be produced in the housing 1826 so as to open the valve 1830 and allow patient fluid to enter the housing 1826 through the open port 1828. The negative pressure further allows the withdrawal of patient fluid into the flexible member and into a collection unit.

Figure 20A:
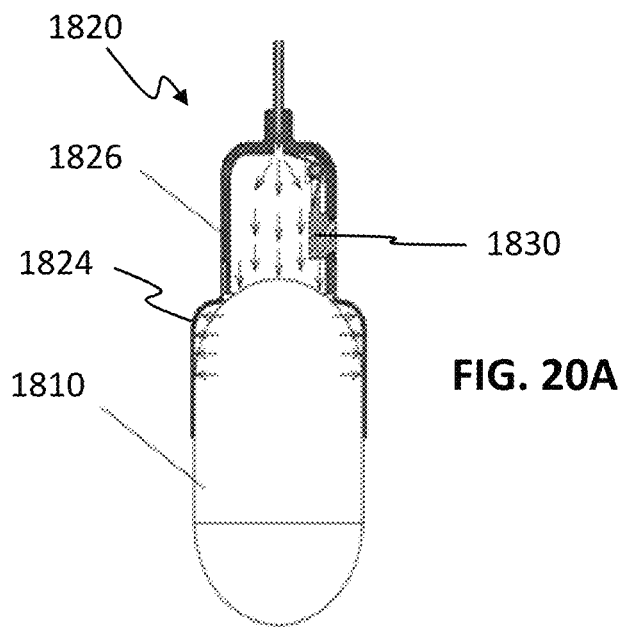
FIGS. 20A and 20B are illustrative schematics depicting disengagement between the capsule endoscope and the tether variation depicted in FIGS. 18A and 18B.
Figure 20B:
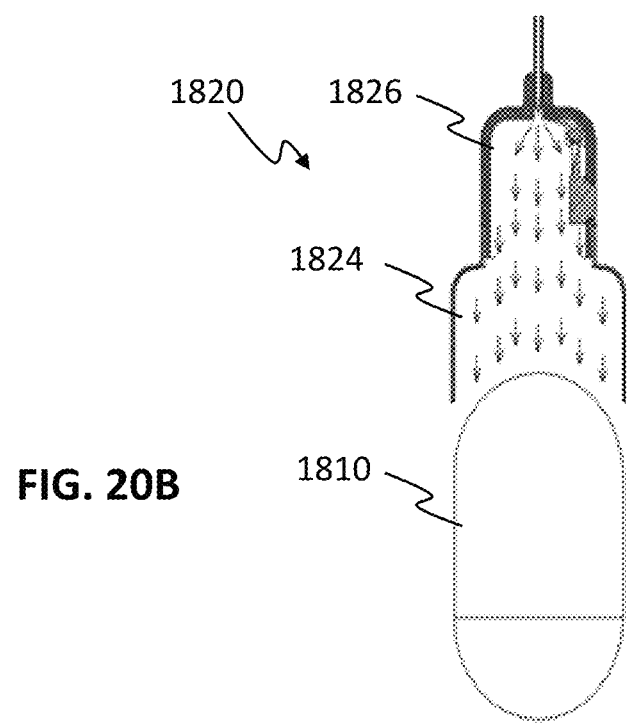

FIGS. 20A and 20B illustrate an exemplary process for disengaging the capsule endoscope 1810 from the tether 1820. As shown in FIG. 20A, a positive pressure may be introduced through the lumen of the flexible member and into the housing 1826 (e.g., with a syringe, pump, or other suitable pressure source). The pressure increase in the chamber may close the valve 1830 (if previously open). Similar to that described above with respect to FIG. 16B, further increased pressure within the housing may cause the flexible sheath 1824 to radially expand and reduce the friction force F1, and/or generate a forward/distal thrust force urging the capsule endoscope distally, Accordingly, as shown in FIG. 20B, such increased pressure within the housing 1826 may cause the capsule endoscope 1810 to disengage from and become released from the sheath 1824 of the tether. The released capsule endoscope may, for example, then by passed by the patient naturally through the digestive tract.

Figure 21A:
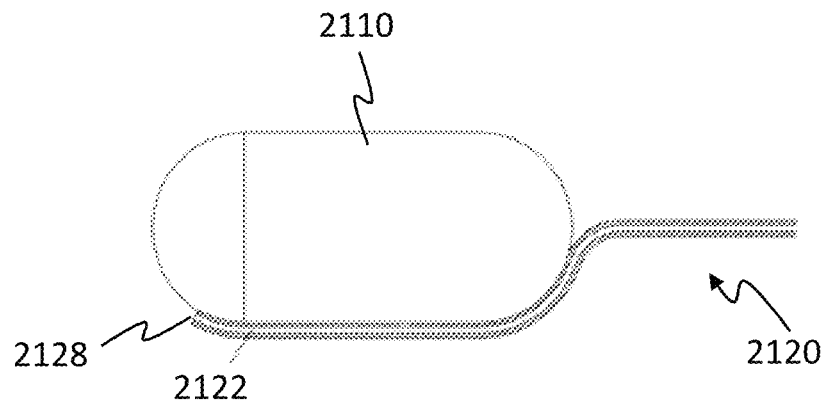
FIGS. 21A and 21B are illustrative schematics of an exemplary variation of a tether variation coupled directly to a capsule endoscope.

In some variations, an endoscopic system may include a port on the flexible member. For example, as shown in FIG. 21A, an exemplary variation of a tether 2120 may include a flexible member 2122 having a port 2128 on its distal end. The flexible member 2122 may be coupled to a capsule endoscope 2110 (e.g., an outer housing of a capsule endoscope including a distal imaging system in its distal end, and/or a proximal imaging system in its proximal end, as described above). For example, as shown in FIG. 21A, a longitudinal segment of the flexible member may be longitudinally coupled to the capsule endoscope 2110. The flexible member 2122 may be coupled to the capsule endoscope 2110 in any suitable manner. For example, the flexible member 2122 may be bonded to the capsule endoscope 2110 with a suitable epoxy. As another example, the flexible member 2122 may be fed through one or more fittings (e.g., eyes or rings) arranged along an outer surface of the capsule endoscope 2110 and secured axially with epoxy and/or with a flange or the like. Furthermore, although FIG. 21A depicts the flexible member 2122 as extending substantially in a straight line, in other variations the flexible member 2122 may traverse the capsule endoscope 2110 in any suitable manner (e.g., serpentine, helical, etc.). As yet another example, at least a portion of the flexible member 2122 may be co-extruded with a feature of the capsule endoscope 2110 so as to be integrally formed.

Figure 21B:
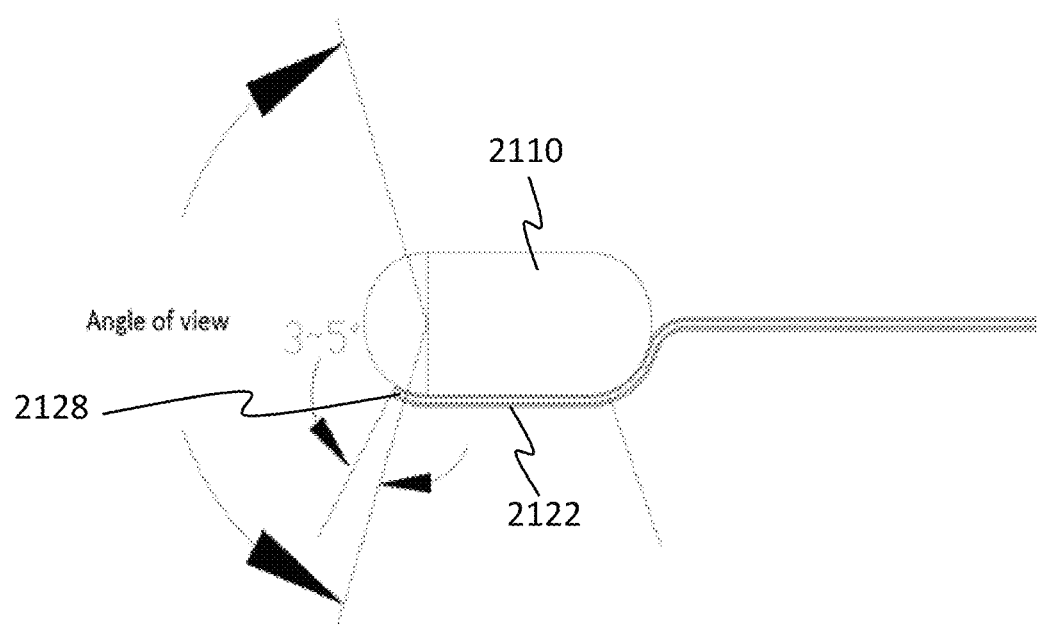
Figure 21C:
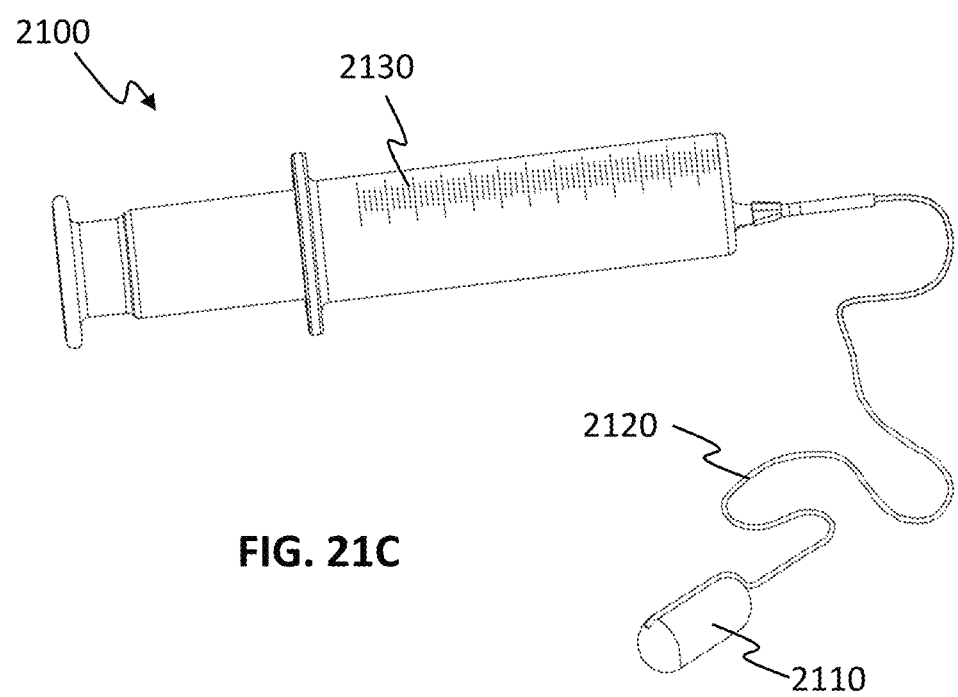
FIG. 21C is an illustrative schematic of a tethered system include the tether variation depicted in FIGS. 21A and 21B.

As shown in FIG. 21B, in some variations the distal end of the flexible member 2122 may be arranged such that port 2128 is visible within the distal imaging system's field of view, which may, for example, enable the distal imaging system to observe activity around the port 2128 (e.g., liquid entering the flexible member through the port 2128 during liquid biopsy, liquid exiting the flexible member through the port 2128 during drug delivery, etc.). In an exemplary variation as shown in FIG. 21C, the distal end of the flexible member 2122 may extend approximately between about 3 degrees and 5 degrees into the distal imaging system's angle of view such that the port 2128 is within the field of view. However, the distal end of the flexible member 2122 may extend further (e.g., between about 5 degrees and 10 degrees, or greater) or less (e.g., between about 1 degree and about 3 degrees) in other variations.

As shown in FIG. 21B, in a system 2100, a capsule endoscope 2110 may be coupled to a tether (to flexible member 2122 having a port 2128) as described above. The capsule endoscope 2110 may, for example, be similar to the capsule endoscope 600 described above with reference to FIGS. 6A-6C having proximal and distal imaging systems, except that the capsule endoscope 2110 may omit a port. The flexible member 2122 may be coupled to a pressure modulator 2130 (e.g., pressure source or vacuum source, such as a syringe or pump).

Figure 22A:
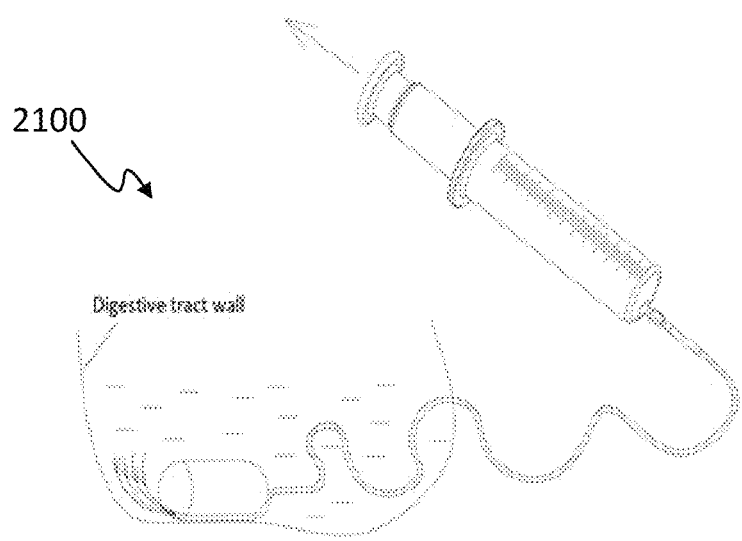
FIG. 22A is an illustrative schematic depicting a method for performing liquid biopsy using the tether variation depicted in FIGS. 21A and 21B.

FIG. 22A illustrates an exemplary use of the system 2100 in which the system 2100 is advanced to a fluid environment (e.g., in pancreatic juice). The distal imaging system of the capsule endoscope 2110 may be used to observe patient fluid in the surroundings of the capsule endoscope, thereby confirming the presence of patient fluid adjacent the port 2128. When presence of sufficient patient fluid is confirmed (e.g., submersion of the port 2128 in the patient fluid is determined), a negative pressure provided by the pressure modulator 2130 may be formed in the flexible member 2122 and in the port 2128. This negative pressure causes the patient fluid to be drawn into the port 2128, the flexible member 2122, and out of the patient into a collection (e.g., syringe).

Figure 22B:
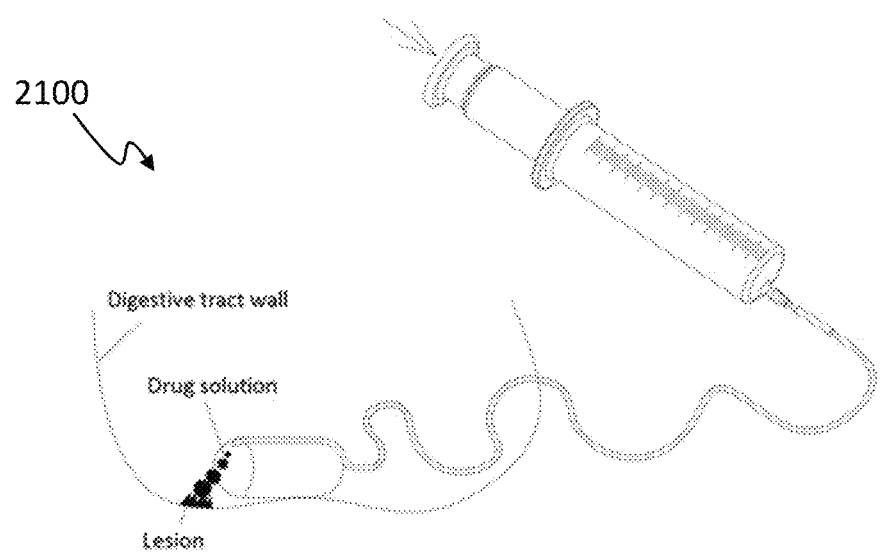
FIG. 22B is an illustrative schematic depicting a method for performing drug delivery using the tether variation depicted in FIGS. 21A and 21B.

Additionally, as shown in FIG. 22B, the system 2100 may be advanced to a region of interest including a lesion. The distal imaging system in the capsule endoscope 2110 may be used to observe the lesion and confirm that the port 2128 is in a suitable location and/or that the capsule endoscope is in a suitable orientation for treatment. When the suitable location and/or orientation is determined, a drug (e.g., a therapeutic agent) may be delivered in the flexible member 2122, and a positive pressure provided by the pressure modulatory may be formed in the flexible member 2122 and the port 2128. This positive pressure causes the drug to be urged down the flexible member and out of the port toward the lesion.

In some variations, as shown in FIGS. 23A and 23B, the capsule endoscope 2110 may have a center of gravity that is biased toward the side of the capsule endoscope including the port 2128, such that the gravity may tend to help the submersion of the port 2128 in pooled fluid for obtaining liquid biopsy. As shown in FIGS. 23A and 23B, the center of gravity may be radially offset from the centroid, such as toward the port side of the capsule endoscope 2110. The center of gravity may be adjusted appropriately by, for example, distributing more weight (e.g., magnet 2140, which may be relatively dense) toward the port side of the capsule endoscope 2110. However, the center of gravity may additionally or alternatively be adjusted in other suitable ways, such as a non-uniform distribution of housing material (e.g., thickness of the housing may be greater, or the housing may have a heavier material on a side proximate the port 2128). Additionally or alternatively, a relatively buoyant element or feature (e.g., an air-containing compartment) may be located on an opposing side of the capsule endoscope relative to the port 2128. As shown in FIG. 23C, the bias in center of gravity and/or effect of buoyancy may tend to cause the capsule endoscope 2110 to rotate so as to submerge the distal end of the flexible member 2122 (and the port 2128) when in patient fluid.

FIGS. 24A-24C illustrate another exemplary variation of a tether 2420, which may be similar to the tether 2120 described above with reference to FIGS. 21-23 except as described below. While the tether 2120 described above is coupled directly to the capsule endoscope, the tether 2420 may be coupled directly to a clamp 2424. For example, a longitudinal segment of the flexible member 2422 may couple to the clamp 2424 in any suitable manner. The clamp 2424 may include a sheath or suction cup similar to that described above, which may, for example, leave a distal imaging assembly of the capsule endoscope substantially unobstructed. The port 2328 on a distal end of the flexible member 2422 may be in the field of view of the distal imaging assembly, similar to that described above with reference to FIG. 21C. As shown in FIGS. 24B and 24C, the clamp 2424 may be configured to receive the capsule endoscope 2410. Furthermore, like the capsule endoscope 2110, the capsule endoscope 2410 may include a center of gravity that is biased toward the side of the clamp 2424 including the port 2328.

Magnetic Control System

As described above, in some variations, the capsule endoscope may be controlled at least in part through a magnetic control system. For example, a capsule endoscope (e.g., as shown in FIGS. 2B and 2C, FIGS. 5B and 5C, FIG. 6C referenced above) may include one or more internal magnets that may be controlled by an external magnetic control system. The internal magnets may, for example, be permanent magnets (e.g., rare earth magnets, such as neodymium magnets).

In some variations, a capsule endoscope may include at least one internal magnet configured to enable six degrees of freedom (translation and rotation in each of three axes). For example, a capsule endoscope may include an internal magnetic assembly including a first magnet and a second magnet coupled to the first magnet, where the first magnet has a polarity oriented along a first direction and the second magnet has a polarity oriented along a second direction different from the first direction (e.g., the second direction may be perpendicular to the first direction). The external magnetic control system may provide magnetic forces that act upon the first and second magnets in tandem, thereby enabling both translation and rotation along three axes. Thus, the internal magnet(s) may allow complex and fine maneuvering of the capsule endoscope by an external magnetic control system, including maintaining a point position of the capsule endoscope while rotating the capsule endoscope around its longitudinal axis (a roll movement), as described below.

Figure 27B:
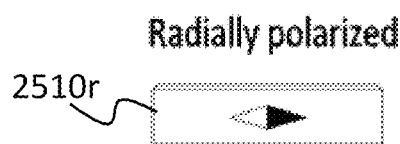
FIGS. 27A-27C are perspective, side, and top schematic views, respectively, of a radially polarized magnet.
Figure 27C:
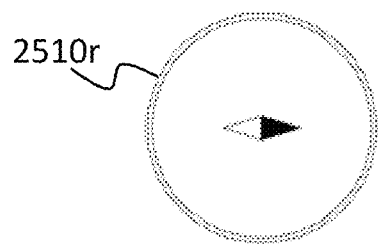
Figure 27A:
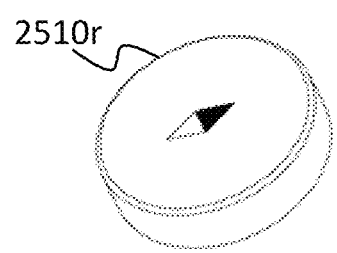
Figure 28B:
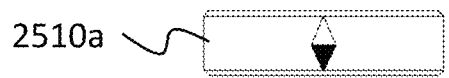
FIGS. 28A-28C are perspective, side, and top schematic views, respectively, of an axially polarized magnet.
Figure 28C:
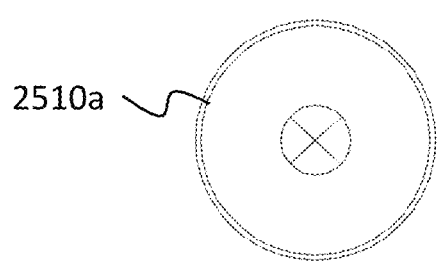
Figure 28A:
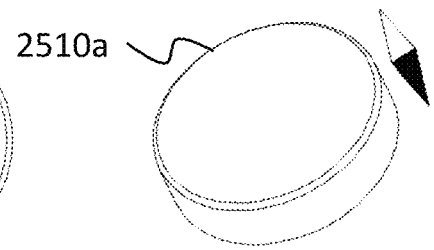

FIGS. 25A and 25B depicts one exemplary variation of an internal magnetic assembly 2500 including a first magnet 2510$r$ and a second magnet 2510$a$, where the first magnet 2510$r$ may be radially polarized (FIGS. 27A-27C), and the second magnet 2510$a$ may be axially polarized (FIGS. 28A-28C). The first and second magnets may be generally disc-shaped, and coupled to each other along adjacent faces (e.g., with epoxy or other adhesive, fasteners, etc.) such that their polarities are orthogonal to each other. Although FIGS. 25A and 25B depict first magnet 2510$r$ and the second magnet 2510$a$ as disc-shaped, though may alternatively be any suitable shape. As shown in FIGS. 25A and 25B, the first and second magnets may be approximately the same size and shape, though in other variation they may differ in size (e.g., width or diameter, thickness, etc.) and/or shape. FIGS. 26A and 26B depict another exemplary variation of an internal magnetic assembly 2600 including a first magnet 2510$r$ and a second magnet 2510$a$. The internal magnetic assembly 2600 is similar to the internal magnetic assembly 2500, except that in the internal magnetic assembly 2500 (FIGS. 25A-25B) the second magnet 2510$a$ is arranged with its north pole pointing away from the first magnet 2510$r$, while in the internal magnetic assembly 2600 (FIGS. 26A-26B) the second magnet 2510$a$ is arranged with its north pole pointing toward the first magnet 2510$r$.

Figure 29:
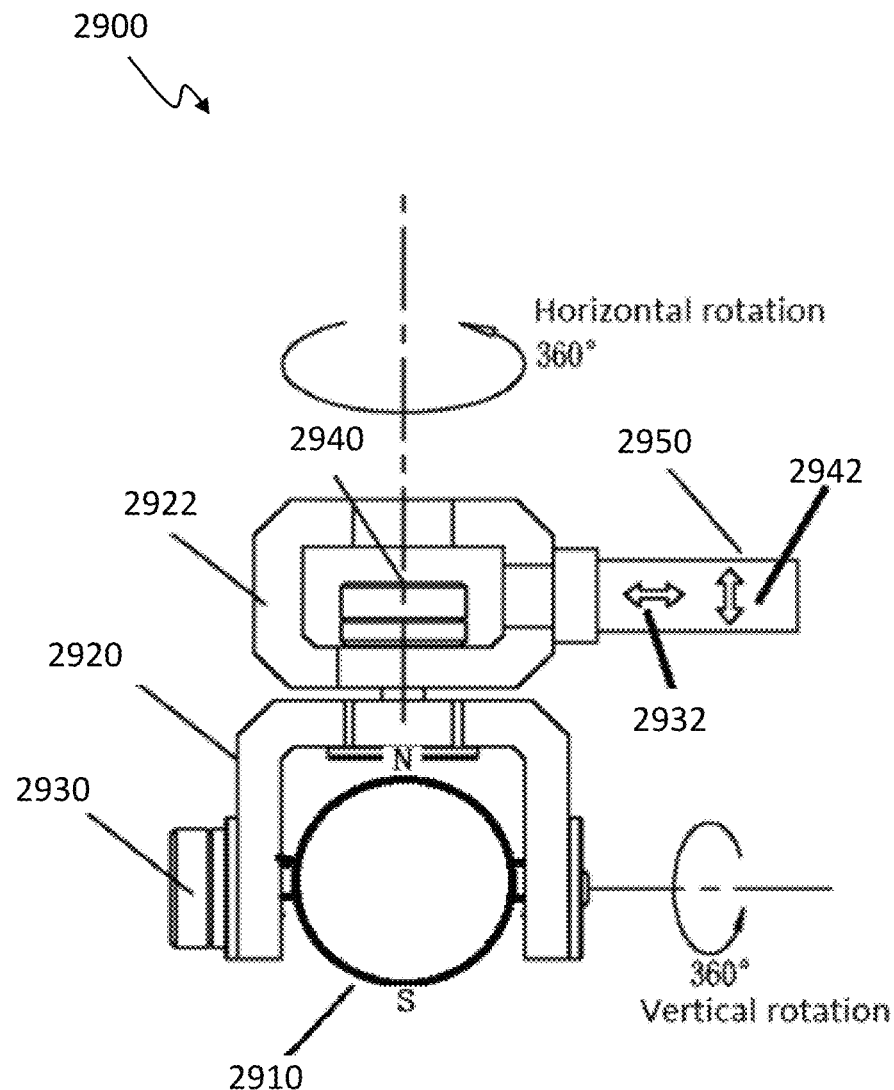
FIG. 29 is an illustrative schematic depicting an exemplary variation of an external magnetic control system.

The posture (position, orientation, etc.) of the capsule endoscope may be controlled at least in part with an external magnetic control system, such as the external magnetic control system 2900 shown in FIG. 29. In some variations, the external magnetic control system 2900 may be similar to that described in U.S. Pat. Nos. 10,076,234 and 10,070,854, each of which is hereby incorporated in its entirety by this reference.

For example, the external control system 2900 may include a spherical magnet 2910 (e.g., permanent magnet or electromagnet) controllable within a frame structure to provide a rotatable external magnetic field. Directional changes of the external magnetic field may cause the internal magnetic assembly (and the capsule endoscope) to change position and/or orientation.

The spherical magnet 2910 may be actuated to translate and/or rotate in three dimensional space. For example, the spherical magnet 2910 may be coupled to a lower frame portion 2920 of the frame structure, and the frame structure may be translated vertically and/or horizontally in frontward-backward and/or left-right directions (e.g., via an actuated arm, or along tracks, etc.). The spherical magnet 2910 may be mounted on a shaft that is rotatable through actuation of a first motor 2930, such that the first motor 2930 may provide vertical rotation of the spherical magnet 2910 around a horizontal axis. Additionally, the lower frame 2920 (to which the spherical magnet 2910 may be mounted) may be rotatable relative to an upper frame portion 2922 of the frame structure through actuation of a second motor 2940, such that the second motor 2940 may provide horizontal rotation of the spherical magnet 2910 around a vertical axis. In other variations, translating and/or rotating the spherical magnet 2910 may be performed in any suitable manner. In some variations, a user interface controls (e.g., control handle 2950) may be coupled to the frame structure to enable operation of such movements. For example, as shown in FIG. 29, the control handle 2950 may include one or more buttons (e.g., button 2932 which may control horizontal rotation, button 2942 which may control vertical rotation), knobs, or other suitable controls. Further details of an exemplary operation of the magnetic control system to manipulate the spherical magnet for control of a magnet internal to a patient are described in U.S. Pat. Nos. 10,076,234 and 10,070,854, which were incorporated above.

Figures 30A, 30B:
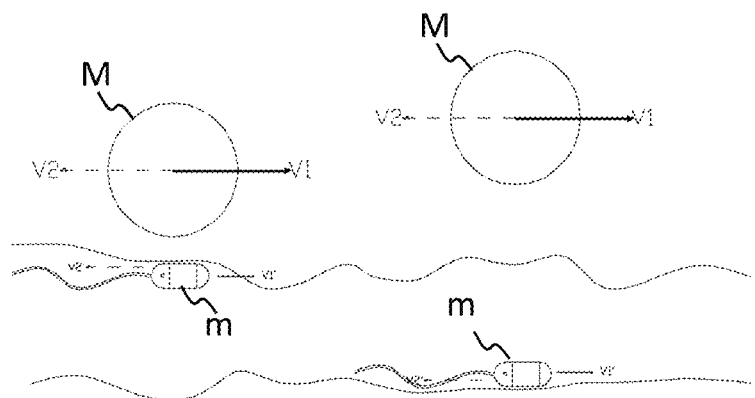
FIGS. 30A and 30B, FIGS. 31A and 31B, and FIGS. 32A and 32B are illustrative schematics depicting control of a capsule endoscope through motions of an external magnetic control system.
Figures 31A, 31B:
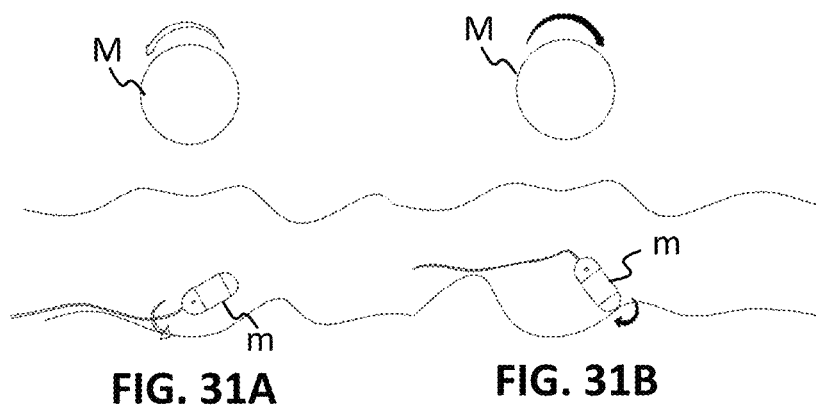
Figures 32A, 32B:
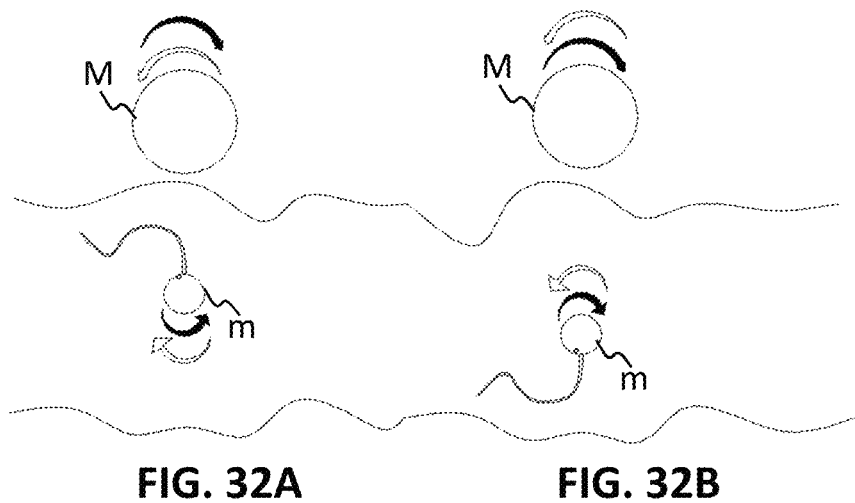

FIGS. 30A-32B illustrate exemplary controlled movements of the capsule endoscope using the external control system. For example, as shown in FIGS. 30A and 30B, translational movement of the external magnet (M) results in corresponding translational movement of the internal magnet assembly (m) in the capsule endoscope. Furthermore, the distance between the external magnet (M) and the internal magnet assembly (m) in the patient body may be controlled by moving the external magnet (M) closer to (FIG. 30A) or farther from (FIG. 30B) the patient body. Additionally, as shown in FIG. 31A, pitch movement of the external magnet (M) may result in a corresponding pitch movement of the internal magnet assembly (m). Similarly, as shown in FIG. 31B, a yaw movement of the external magnet (M) may result in a corresponding yaw movement of the internal magnet assembly (m). Furthermore, as shown in FIGS. 32A and 32B, a combined set of simultaneous pitch and yaw movements of the spherical external magnet (M) may result in a corresponding roll movement of the internal magnet assembly (m) in either direction. Accordingly, translational and rotational movement of the capsule endoscope may be controlled due to interactions between the magnetic control system and the internal magnetic assembly.

Pressure Modulator

As described above, systems for accessing a patient may include at least one pressure modulator coupled to the tether and configured to decrease pressure and/or increase pressure within the tether for withdrawing and/or urging fluid through a port (e.g., in the tether, in a capsule endoscope, etc.). The pressure modulator may be a pressure source and/or a vacuum source arranged in fluidic communication with the tether (e.g., a lumen of a flexible member in the tether).

Figure 33A:
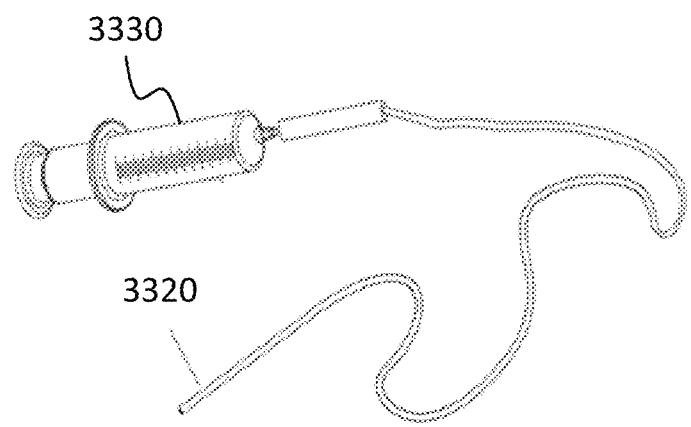
FIGS. 33A and 33B are illustrative schematics depicting exemplary variations of a pressure modulator including a syringe and a pump, respectively.

For example, as shown in FIG. 33A, the pressure modulator may include a syringe 3330 that is fluidically coupled to a flexible member of a tether 3320. The plunger of the syringe 3330 may be withdrawn in order to create negative pressure in the tether and draw fluid (e.g., for liquid biopsy) through a port (not shown) and through the tether 3320. The withdrawn fluid may be collected with the syringe 3330 and/or collected with another container fluidically connected in-line with the tether, similar to that described below with respect to FIG. 33B. Furthermore, the plunger of the syringe 3330 may be depressed in order to create positive pressure in the tether, such as to urge fluid (e.g., for drug delivery, for capsule endoscope disconnection from a clamp member as described above, etc.) through the tether 3320 and a port (not shown).

Figure 33B:
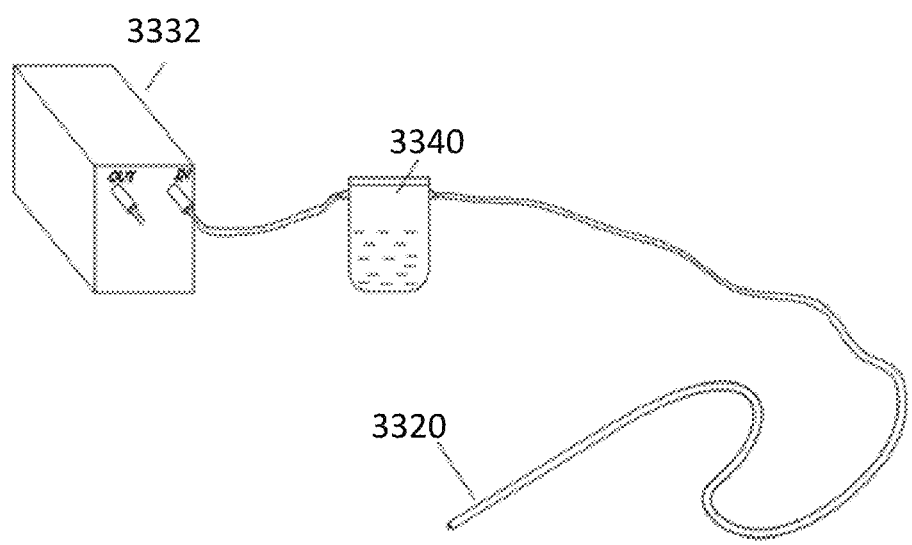

As another example, as shown in FIG. 33B, the pressure modulatory may include a vacuum pump 3332 that is fluidically coupled to a flexible member of a tether 3320. A collection unit 3340 (e.g., container) may be fluidically connected in-line with the tether, such that when the vacuum pump 3332 is turned on and creates negative pressure in the tether to withdraw fluid (e.g., liquid biopsy) into the tether 3320, the withdrawn fluid is transferred into the collection unit 3340. Furthermore, a pressure pump may be similarly fluidically coupled to the tether 3320 to create a positive pressure in the tether (e.g., for drug delivery, for capsule endoscope disconnection from a clamp member as described above, etc.). Alternatively, a pump capable of selectively being a vacuum pump or a pressure pump may be coupled to the tether, and toggled between vacuum and pressure modes.

Figure 34A:
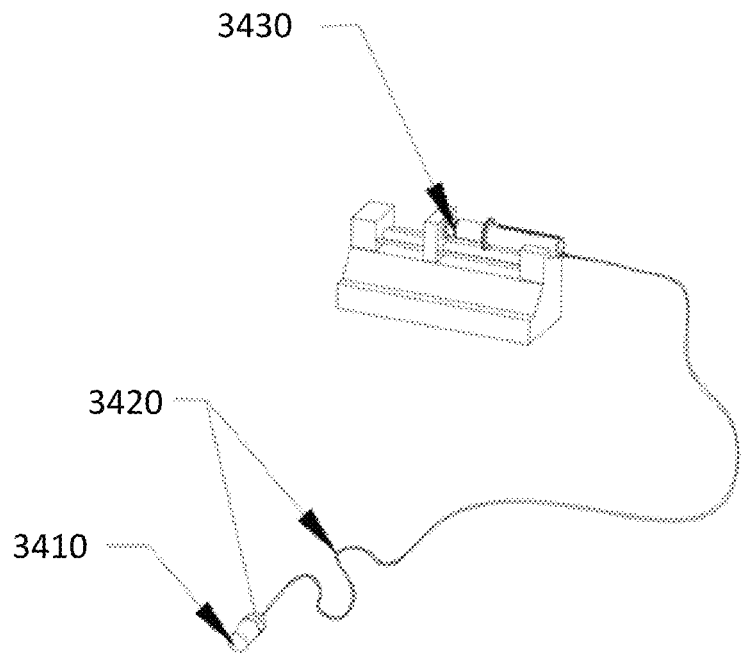
FIG. 34A is an illustrative schematic depicting another exemplary variation of a pressure modulator including a microflow syringe pump.
Figure 34B:
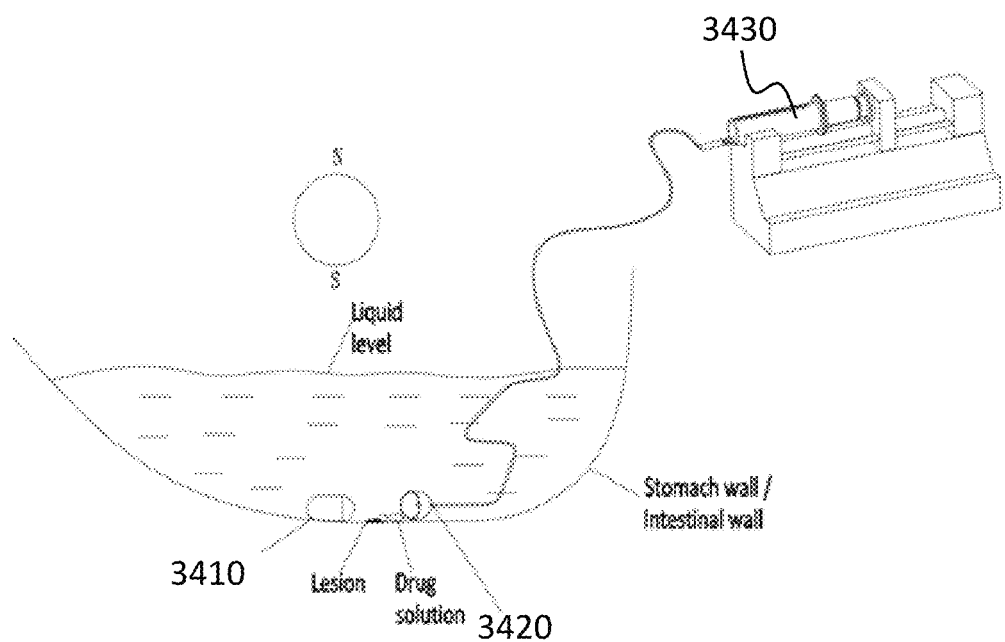
FIG. 34B is an illustrative schematic of a method of using the pressure modulator depicted in FIG. 34A.

In another exemplary variation as shown in FIGS. 34A and 34B, a system for accessing a patient may include a pressure modulator including a microflow syringe pump 3430. The microflow syringe pump may be coupled to the tether 3420 as described above, and the tether 3420 may be coupled to a capsule endoscope 3410 in any suitable manner such as those variations described above. After advancing the capsule endoscope 3410 to a region of interest (e.g., lesion) and enabling a port to be proximate the region of interest, the microflow syringe pump 3430 may be actuated to deliver a drug through the tether 3420 and the port (not labeled). The microflow syringe pump 3430 (in combination with the capsule endoscope and tether arrangements such as those described herein) may achieve a long-acting therapeutic effect by continuously releasing micro-doses of drug to the region of interest. In some variations, the capsule endoscope may be controlled (e.g., by an external magnetic control system as described above) such that its imaging system observes the delivery of the drug through the port to the region of interest. After treatment is complete, the capsule endoscope may be released from the tether and passed by the patient's gastrointestinal tract, and the tether may be withdrawn and removed from the patient.

Methods for Accessing a Patient

Various methods for accessing a patient may include using one or more capsule endoscopes, such as any of the capsule endoscope variations described above. For example, in some variations, a method for obtaining one or more substances from a patient may include advancing a capsule endoscope into a body cavity (e.g., gastrointestinal tract) of a patient, where the capsule endoscope is coupled to a tether including a flexible member with a lumen, positioning the capsule endoscope at a region of interest, and withdrawing a patient sample from the region of interest through the lumen (e.g., by forming a negative pressure in the lumen). The capsule endoscope may be advanced with an external magnetic control system and/or through peristalsis, etc. The patient sample may be withdrawn through a port that is in fluidic communication with the lumen. The port may be located in any one or more structures in or around the capsule endoscope and/or tether, as described above with respect to various tethered capsule endoscope variations.

Generally, the region of interest may be any suitable location in the gastrointestinal tract and/or other features of the digestive system, such as the mouth, esophagus, stomach, small intestine, large intestine, anus, liver, pancreas, gallbladder, and the like. However, the region of interest may be in any suitable body cavity or other region of a patient.

The method may be used to obtain patient samples that are fluid samples from the body (e.g., liquid biopsy). For example, one exemplary application of the method is obtaining a sample of pancreatic juice from a patient, where the pancreatic juice may, for example, be analyzed for mutations indicating the presence of cancer. Another exemplary application of the method is obtaining a sample of intestinal flora (e.g., bacteria) which may, for example, be analyzed to assess gut health. While any suitable amount of fluid may be withdrawn (e.g., depending on sample availability or the application of the method), in some variations the method may include withdrawing between about 0.5 mL and about 15 mL, between about 0.5 mL and about 10 mL, between about 0.5 and about 5 mL, between about 5 mL and about 10 mL, between about 1 mL and about 3 mL, more than about 10 mL, or more than about 15 mL, etc.

Additionally or alternatively, the method may include obtaining any suitable matter from the body cavity of the patient. For example, the method may be used to obtain particle patient samples and/or suitable foreign particles that may be residing in fluid or may be small and/or light enough to be suctioned through the port. Exemplary particles may include, for example, cancer cells, debris and/or exosomes shedding from cancer cells and/or immune cells, other suitable biomarkers, etc.

As another example, in some variations, a method for delivering one or more substances may include advancing a capsule endoscope into a body (e.g., gastrointestinal tract) of a patient, where the capsule endoscope is coupled to a tether including a flexible member with a lumen, positioning the capsule endoscope at a region of interest, and administering a therapeutic substance to the region of interest through the lumen (e.g., by forming a positive pressure in the lumen). The capsule endoscope may be advanced with an external magnetic control system and/or through peristalsis, etc. The drug may be delivered through a port that is in fluidic communication with the lumen. The port may be located in any one or more structures in or around the capsule endoscope and/or tether, as described above with respect to various tethered capsule endoscope variations. In some variations, the capsule endoscope may remain static in a single location and orientation during delivery of the substance, while in other variations the capsule endoscope may be moved while delivering the substance (e.g., rotating about an axis, translating, etc.) to coat or spray a wider surface area of treatment.

The method may be used to deliver one or more therapeutic substances to the body cavity of the patient. For example, one exemplary application of the method is delivering one or more drugs to an intestinal region of interest for treatment of inflammatory bowel disease (IBD) such as Crohn's disease or ulcerative colitis. Exemplary drugs that may be delivered include thrombin, norepinephrine, batroxobin, etc., as well as suitable drug combinations (e.g., about 240,000 units gentamicin combined with between about 50 ml to about 100 ml of 5% GNS, between about 5 mg to about 10 mg dexamethasone, and about 1.2 g of metronidazole). As another example, the method may be used to deliver one or more drugs to an esophageal region to treat one or more lesions, such as in target therapy using nanoparticles such as multimodality nanoparticles suitable for imaging, characterization, and therapy, etc. (e.g., for SERS optical biopsy, photothermal therapy, photodynamic therapy, etc.). Exemplary particles for these applications include gold or silver nanoparticles, carbon nanotubes, and gold nanorods, etc. As yet another example, the method may be used to spray a drug or other therapeutic substance, such as for stopping or reducing gastrointestinal bleeding (e.g., in the esophagus, stomach, small bowel, colon, etc.). Exemplary drugs for spraying include Hemospray® Endoscopic Hemostat (Cook Medical, Winston-Salem, North Carolina, USA), Ankaferd Blood Stopper (Ankaferd Health Products, Ltd., Istanbul, Turkey), EndoClot® Polysaccharide Hemostatic System (EndoClot Plus, Inc., Santa Clara, California, USA), and the like.

In yet other variations, the methods described herein may be used to deliver and/or withdraw other suitable substances using capsule endoscope systems such as those described herein. For example, the methods may be used to release fluid (e.g., gas such as air or nitrogen, liquid such as saline or water, etc.) via a capsule endoscope system with a port, which may be used to inflate at least a portion of the gastrointestinal tract (e.g., stomach, small intestine, large intestine, colon, etc.). Such inflation may be useful, for example, to aid visibility for imaging, etc. within the gastrointestinal tract using the same endoscope device or other suitable imaging device. As another example, the methods may be used for facilitating nanoscale drug delivery by releasing nanoparticle drug carriers (e.g., liposomes, carbon nanotubes, dendrimers, polymeric nanoparticles, gold-based nanoparticles, etc.). Suitable drugs to be carried may include anti-inflammatory agents, anti-infective agents, and the like.

In some variations, the same capsule endoscope during a procedure may be used for both obtaining a patient sample and delivering a drug. For example, after advancing a capsule endoscope to a region of interest, a negative pressure may be formed in the tether to withdraw a patient sample or other matter through the port, and a positive pressure may subsequently be formed in the tether to deliver a drug or other matter through the port. Alternatively, a positive pressure may be formed before forming a negative pressure.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A system, comprising:
a capsule endoscope comprising an imaging system; and
a tether comprising:
a clamp configured to engage the capsule endoscope; and
a flexible member comprising a lumen,
wherein the clamp comprises a port in fluidic communication with the lumen and with an environment outside and around the clamp while the clamp is engaged with the capsule endoscope, and
wherein the lumen of the flexible member terminates at the port of the clamp and is coaxial therewith.

2. The system of claim 1, wherein the imaging system comprises a first lens on a proximal portion of the capsule endoscope.

3. The system of claim 2, wherein the imaging system comprises a second lens on a distal portion of the capsule endoscope.

4. The system of claim 1, wherein the clamp comprises a sheath configured to surround at least a portion of the capsule endoscope.

5. The system of claim 4, wherein the clamp comprises an anchor member coupling the sheath and the flexible member.

6. The system of claim 5, wherein the port is on the anchor member and axially offset from a proximal portion of the capsule endoscope.

7. The system of claim 5, wherein the anchor member comprises one or more arcuate structures.

8. The system of claim 4, wherein the clamp comprises a housing defining a chamber between the sheath and the flexible member, wherein the housing comprises the port.

9. The system of claim 8, wherein the housing further comprises a valve.

10. The system of claim 1, further comprising at least one of a pressure source and vacuum source arranged in fluidic communication with the lumen.

11. The system of claim 10, wherein the at least one of a pressure source and vacuum source comprises a syringe.

12. The system of claim 10, wherein the at least one of a pressure source and vacuum source comprises a pump.

13. The system of claim 1, wherein the clamp is configured to releasably engage the capsule endoscope.

14. The system of claim 1, wherein translational and rotational movement of the capsule endoscope is magnetically controllable with an external magnetic control system.

15. The system of claim 1, wherein the tether is configured to transport a fluid patient sample through the lumen of the flexible member from a region of interest in a patient to a collection unit.

16. The system of claim 1, wherein the tether is configured to transport a drug through the lumen of the flexible member from a drug source to a region of interest in a patient.

17. The system of claim 1, wherein the flexible member has a Shore A hardness between about 35 and about 65.

18. The system of claim 1, wherein the entire tether is flexible.

19. The system of claim 1, wherein the tether is made entirely from a silicone elastomer.

20. The system of claim 1, wherein a center of gravity of the capsule endoscope is biased toward the port.

21. The system of claim 1, wherein the clamp comprises a window region configured to provide visual clearance for the imaging system of the capsule endoscope.

22. The system of claim 15, wherein the port is configured to be submerged at the region of interest within a fluid to be biopsied, the fluid to be biopsied comprising the fluid patient sample.

* * * * *